US005461050A

United States Patent [19]

Janssens et al.

[11] Patent Number: 5,461,050

[45] Date of Patent: Oct. 24, 1995

[54] IMIDAZO[1,2-A](PYRROLO, THIENO OR FURANO) [3,2A-D]AZEPINE DERIVATIVES, COMPOSITIONS AND METHODS OF USE

[75] Inventors: Frans E. Janssens, Bonheiden; Gaston S. M. Diels, Ravels; Joseph E. Leenaerts, Rijkevorsel; Ludwig P. Cooymans, Beerse, all of Belgium

[73] Assignee: Janssen Pharmaceutica N.V., Beerse, Belgium

[21] Appl. No.: 150,121

[22] PCT Filed: Jun. 9, 1992

[86] PCT No.: PCT/EP92/01331

§ 371 Date: Nov. 29, 1993

§ 102(e) Date: Nov. 29, 1993

[87] PCT Pub. No.: WO92/22553

PCT Pub. Date: Dec. 23, 1992

[51] Int. Cl.[6] .......................... A61K 31/55; C07D 487/14; C07D 491/147; C07D 495/14

[52] U.S. Cl. .......................... 514/214; 540/578

[58] Field of Search .......................... 540/578; 514/214

[56] References Cited

U.S. PATENT DOCUMENTS 5,008,268 4/1991 Janssens et al. .......................... 514/272

FOREIGN PATENT DOCUMENTS 0000716 2/1979 European Pat. Off. .

*Primary Examiner*—Philip I. Datlow

*Attorney, Agent, or Firm*—Charles J. Metz

[57] ABSTRACT

The present invention is concerned with novel imidazo[1,2-a](pyrrolo, thieno or furano)[3,2-d]azepines of formula (I)

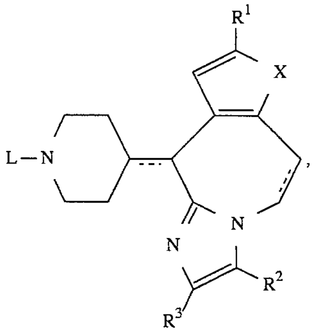

the pharmaceutically acceptable addition salts and stereochemically isomefic forms thereof, wherein each of the dotted lines independently represents an optional bond;

$R^1$ represents hydrogen, $C_{1-4}$ alkyl, halo, ethenyl substituted with hydroxycarbonyl or $C_{1-4}$ alkyloxycarbonyl, hydroxy $C_{1-4}$ alkyl, formyl, hydroxycarbonyl or hydroxycarbonyl $C_{1-4}$ alkyl;

$R^2$ represents hydrogen, $C_{1-4}$ alkyl, ethenyl substituted with hydroxycarbonyl or $C_{1-4}$ alkyloxycarbonyl, $C_{1-4}$ alkyl substituted with hydroxycarbonyl or $C_{1-4}$ alkyloxycarbonyl, hydroxy $C_{1-4}$ alkyl, formyl or hydroxycarbonyl;

$R^3$ represents hydrogen, $C_{1-4}$ alkyl, hydroxy $C_{1-4}$ alkyl, phenyl or halo;

L represents hydrogen; $C_{1-6}$ alkyl; $C_{1-6}$ alkyl substituted with one substituent selected from the group consisting of hydroxy, halo, $C_{1-4}$ alkyloxy, hydroxycarbonyl, $C_{1-4}$ alkyloxycarbonyl, $C_{1-4}$ alkyloxycarbonyl $C_{1-4}$ alkyloxy, hydroxycarbonyl $C_{1-4}$ alkyloxy, $C_{1-4}$ alkyloxycarbonylamino, $C_{1-4}$ alkylaminocarbonyl, $C_{1-4}$ alkylaminocarbonylamino, $C_{1-4}$ alkylaminothiocarbonylamino, aryl, aryloxy and arylcarbonyl; $C_{1-6}$ alkyl substituted with both hydroxy and aryloxy; $C_{3-6}$ alkenyl; $C_{3-6}$ alkenyl substituted with aryl;

L represents a radical of formula —Alk—Y—Het$^1$ (a-1), —Alk—NH—CO—Het$^2$ (a-2) or —Alk—Het$^3$ (a-3); which are useful antiallergic compounds. Compositions comprising said compounds, methods of using, and processes for preparing the same.

16 Claims, No Drawings

IMIDAZO[1,2-A](PYRROLO, THIENO OR FURANO) [3,2A-D]AZEPINE DERIVATIVES, COMPOSITIONS AND METHODS OF USE

CROSS-REFERENCE TO RELATED APPLICATIONS

This application is based upon PCT Application No. PCT/EP 92/01331, filed Jun. 9, 1992, which claims priority from U.S. application Ser. No. 714,487, filed Jun. 13, 1991, now abandoned.

BACKGROUND OF THE INVENTION

In EP-A-0,339,978 there are described (benzo- or pyfido)cyclohepta heterocyclics which are useful as PAF antagonists, antihistaminics and/or anti-inflammatory agents.

In the J. Meal. Chem., 26 (1983), 974–980 there are described some 1-methyl-4-piperidinylidene- 9-substituted pyrrolo[ 2,1-b][3]benzazepine derivatives having neuroleptic properties.

The compounds of the present invention differ structurally from the cited art-known compounds by the fact that the central 7-membered ring invariably contains a nitrogen atom of a fused imidazole ring, and by their favorable antiallergic activity.

DESCRIPTION OF THE INVENTION

The present invention is concerned with novel imidazo [1,2-a](pyrrolo, thieno or furano)[3,2-d]azepines of formula (I)

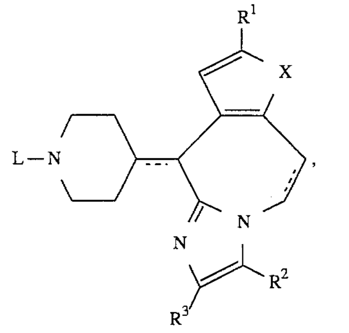

the pharmaceutically acceptable addition salts and stereochemically isomefic forms thereof, wherein each of the dotted lines independently represents an optional bond;

$R^1$ represents hydrogen, $C_{1-4}$ alkyl, halo, ethenyl substituted with hydroxycarbonyl or $C_{1-4}$alkyloxycarbonyl, hydroxy $C_{1-4}$alkyl, formyl, hydroxycarbonyl or hydroxycarbonyl $C_{1-4}$alkyl;

$R^2$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl;

$R^3$ represents hydrogen, $C_{1-4}$alkyl, hydroxy $C_{1-4}$alkyl, phenyl or halo;

L represents hydrogen; $C_{1-6}$alkyl; $C_{1-6}$alkyl substituted with one substiuent selected from the group consisting of hydroxy, halo, $C_{1-4}$alkyloxy, hydroxycarbonyl, $C_{1-4}$alkyloxycarbonyl, $C_{1-4}$alkyloxycarbonyl $C_{1-4}$alkyloxy, hydroxycarbonyl $C_{1-4}$alkyloxy, $C_{1-4}$alkyloxycarbonylamino, $C_{1-4}$alkylaminocarbonyl, $C_{1-4}$alkylaminocarbonylamino, $C_{1-4}$alkylaminothiocarbonylamino, aryl, aryloxy and arylcarbonyl; $C_{1-6}$alkyl substituted with both hydroxy and aryloxy; $C_{3-6}$alkenyl; $C_{3-6}$alkenyl substituted with aryl;

wherein each aryl is phenyl or phenyl substituted with halo, cyano, hydroxy, $C_{1-4}$alkyl, $C_{1-4}$alkyloxy, aminocarbonyl or phenyl substituted with $C_{1-4}$alkyloxycarbonyl or hydroxycarbonyl; or, L represents a radical of formula $—Alk—Y—Het^1$(a-1), $—Alk—NH—CO—Het^2$(a-2)

or $—Alk—Het^3$ (a-3);

wherein Alk represents $C_{1-4}$alkanediyl; Y represents O, S or NH; $Het^1$, $Het^2$ and $Het^3$ each represent furanyl, thienyl, oxazolyl, thiazolyl or imidazolyl each optionally substituted with one or two $C_{1-4}$alkyl substituents; pyrrolyl or pyrazolyl optionally substituted with formyl, hydroxy $C_{1-4}$alkyl, hydroxycarbonyl, $C_{1-4}$alkyloxycarbonyl or with one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy or halo; imidazo[4,5-c]pyridin-2-yl; and $Het^3$ may also represent 4,5-dihydro-5-oxo-1H-tetrazolyl substituted with $C_{1-4}$alkyl, 2-oxo-3-oxazolidinyl, 2,3-dihydro-2-oxo-1H-benzimidazol-1-yl or a radical of formula

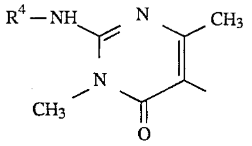

(b-1)

or

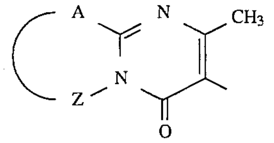

(b-2)

$R^4$ represents hydrogen or $C_{1-4}$alkyl; and

A–Z represents S—CH═CH, S—$CH_2$—$CH_2$, S—$CH_2$—$CH_2CH_2$, CH═CH—CH═CH, $CH_2$—$CH_2$—$CH_2$—$CH_2$, —N($CH_3$)—C($CH_3$)—CH— or —CH—C($CH_3$)—O—;

X represents O, S or $NR_5$; and $R^5$ represents hydrogen, $C_{1-6}$alkyl or $C_{1-4}$alkylcarbonyl.

As used in the foregoing definitions halo defines fluoro, chloro, bromo and iodo; $C_{1-4}$alkyl defines straight and branched chain saturated hydrocarbon radicals having from 1 to 4 carbon atoms such as, for example, methyl, ethyl, propyl, 1-methylethyl, butyl, 1-methylpropyl, 2-methylpropyl and 1,1-dimethylethyl; $C_{1-6}$ alkyl defines $C_{1-4}$ alkyl radicals as defined hereinbefore and the higher homologs thereof having from 5 to 6 carbon atoms such as, for example, pentyl and hexyl; $C_{3-6}$alkenyl defines straight and branched chain hydrocarbon radicals containing one double bond and having from 3 to 6 carbon atoms such as, for example, 2-propenyl, 2-butenyl, 3-butenyl, 2-methyl-2-propenyl, 2-pentenyl, 3opentenyl, 3,3-dimethyl-2-propenyl, hexenyl and the like; $C_{1-4}$alkanediyl defines bivalent straight or branched chain hydrocarbon radicals containing from 1 to 4 carbon atoms such as, for example, methylene, 1,1-ethanediyl, 1,2-ethanediyl, 1,3-propanediyl, 1,4-butanediyl and the like.

The term pharmaceutically acceptable addition salt as used hereinbefore defines the non-toxic, therapeutically active addition salt forms which the compounds of formula (I) may form. The compounds of formula (I) having basic properties may be converted into the corresponding therapeutically active, non-toxic acid addition salt forms by treating the free base form with a suitable amount of an appropriate acid following conventional procedures. Examples of appropriate acids are for example, inorganic acids, for example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The compounds of formula (I) having acidic properties may be converted in a similar manner into the corresponding therapeutically active, non-toxic base addition salt forms. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine. The term pharmaceutically acceptable addition salts also comprises the solvates which the compounds of formula (I) may form, e.g. the hydrates, alcoholales and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some compounds of the present invention may exist in different tautomeric forms and all such tautomeric forms are intended to be included within the scope of the present invention.

Interesting compounds of formula (I) are those compounds wherein:

$R^1$ represents hydrogen;

$R^2$ represents hydrogen, $C_{1-4}$alkyl, hydroxy $C_{1-4}$alkyl, formyl or hydroxycarbonyl;

$R^3$ represents hydrogen, $C_{1-4}$alkyl, hydroxy $C_{1-4}$alkyl, phenyl or halo;

L represents hydrogen; $C_{1-6}$alkyl; $C_{1-6}$alkyl substituted with hydroxy, $C_{1-4}$alkyloxy, $C_{1-4}$alkyloxycarbonylamino, $C_{1-4}$alkylaminocarbonyl, $C_{1-4}$alkylamino-carbonylamino, $C_{1-4}$alkylaminothiocarbonylamino, aryl or aryloxy; $C_{3-6}$alkenyl; $C_{3-6}$alkenyl substituted with aryl;

wherein each aryl is phenyl or phenyl substituted with halo, $C_{1-4}$alkyl or $C_{1-4}$alkyloxy; or, L represents a radical of formula —Alk—Y—$Het^1$ (a-1), —Alk—NH—CO—$Het^2$ (a-2)

or

—Alk—$Het^3$ (a-3);

wherein

Alk represents $C_{1-4}$alkanediyl;

Y represents O, S or NH;

$Het^1$, $Het^2$ and $Het^3$ each represent furanyl, thienyl, pyrrolyl, oxazolyl, thiazolyl or imidazolyl each optionally substituted with one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy or halo; imidazo[4,5-c]pyridin-2-yl; and $Het^3$ may also represent 4,5-dihydro-5-oxo-1H-tetrazolyl substituted with $C_{1-4}$alkyl, 2-oxo-3-oxazolidinyl, 2,3-dihydro-2-oxo-1H-benzimidazol-1-yl or a radical of formula

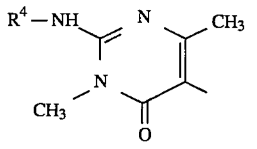

(b-1)

or

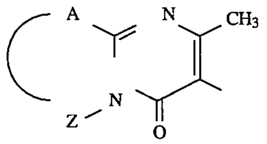

(b-2)

wherein $R^4$ represents hydrogen or $C_{1-4}$alkyl; and

A-Z represents S—CH=CH, S—$CH_2$—$CH_2$, S—$CH_2$—$CH_2$—$CH_2$, CH=CH—CH=CH or $CH_2$—$CH_2$—$CH_2$—$CH_2$;

X represents O, S or $NR_5$; and $R^5$ represents hydrogen or $C_{1-6}$alkyl.

Another group of interesting compounds of formula (I) are those compounds wherein L represents $C_{1-4}$alkyl or $C_{14}$alkyl substituted with hydroxycarbonyl or $C_{1-4}$alkyloxycarbonyl.

A further interesting group of compounds of formula (I) comprises those compounds of formula (I) wherein $R^1$, $R^2$ and $R^3$ represent hydrogen.

Still another group of interesting compounds of formula (I) are those wherein X represents O, S or $NCH_3$.

Yet another group of interesting compounds of formula (I) are those of formula

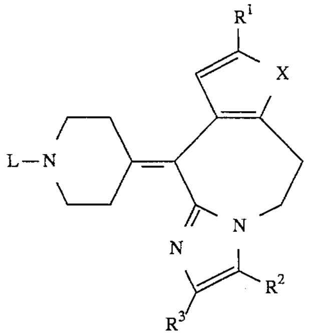

wherein $R^1$, $R^2$, $R^3$, and L are as defined under formula (I).

Preferred compounds are those compounds of formula (I) wherein:

$R^1$ is hydrogen, $C_{1-4}$alkyl, formyl, hydroxy $C_{1-4}$alkyl or hydroxycarbonyl;

$R^2$ is hydrogen or $C_{1-4}$alkyl;

$R^3$ is hydrogen or $C_{1-4}$alkyl, and

L is hydrogen, $C_{1-4}$alkyl, propenyl, hydroxy $C_{1-4}$alkyl, C 14alkylaminocarbonyl-amino $C_{1-4}$alkyl, phenyl $C_{1-4}$alkyl, cyanophenyl $C_{1-4}$alkyl, methoxyphenyl-C 1-4alkyl, hydroxyphenyl $C_{1-4}$alkyl, aminocarbonylphenyl $C_{1-4}$alkyl, hydroxycarbonyl $C_{1-4}$alkyl, $C_{1-4}$alkyloxycarbonyl $C_{1-4}$alkyl, or L is a radical of formula Alk—Y—$Het^1$ (a-1), —Alk—NH—CO—$Het^2$ (a-2)

or

—Alk—$Het^3$ (a-3);

wherein $Het^1$, $Het^2$ and $Het^3$ each represent is thienyl, furanyl, thiazolyl or imidazolyl each optionally substituted with C14alkyl; pyrimidinyl; hydroxypyrimidinyl or pyridinyl; and $Her^3$ may also represent 2-oxo-3ooxazolidinyl, 4,5-dihydro-5-oxo-1H-tetrazolyl substituted with $C_{1-4}$alkyl or a radical of the formula

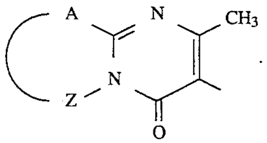

(b-2)

More preferred compounds are those preferred compounds wherein:

$R^1$ is hydrogen, methyl or hydroxycarbonyl;

$R^2$ is hydrogen;

$R^3$ is hydrogen or methyl, and

L is hydrogen, $C_{1-4}$alkyl, propenyl, hydroxy $C_{1-4}$alkyl, methylaminocarbonylamino-$C_{1-4}$alkyl, hydroxycarbonyl $C_{1-4}$alkyl, $C_{1-4}$alkyloxycarbonyl $C_{1-4}$alkyl, cyanophenyl $C_{1-4}$alkyl or L is a radical of formula —Alk—Y—$Het^1$ (a-1), or —Alk—$Het^3$ (a-3);

wherein

Y is S or NH and $Het^1$ is imidazolyl substituted with methyl;

$Het^3$ is 2-oxo-3-oxazolidinyl; 4,5-dihydro-5-oxo-1H-tetrazolyl substituted with ethyl; pyridinyl; thienyl; furanyl or a radical of the formula

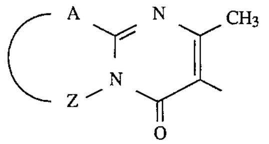

(b-2)

A-Z represents —S—CH=CH—, —S—$(CH_2)_2$—, —S—$(CH_2)_3$— or —$(CH_2)_4$—.

Still more preferred compounds are those more preferred compounds wherein L is $C_{1-4}$alkyl, propenyl or $C_{1-4}$alkyl substituted with hydroxycarbonyl or $C_{1-4}$alkyloxycarbonyl.

The most preferred compounds are:

6,10-dihydro-7-methyl-10-(1-methyl-4-piperidinylidene)-5H, 7H-imidazo[1,2 -a]-pyrrolo[3,2-d] azepine, 5,6-dihydro-10-(1-methyl-4-piperidinylidene)-10H-imidazo[ 1,2-a] thieno-[ 3,2-d]azepine, and 6, 10-dihydro-8-methyl-10-(1-methyl-4-piperidinylidene )-5H- furo[3,2-d]imidazo-[ 1,2-a]azepine, the stereoisomers and the pharmaceutically acceptable acid-addition salts thereof.

In the following paragraphs there are described different ways of preparing the compounds of formula (I). In order to simplify the structural formulae of the compounds of formula (I) and the intermediates intervening in their preparation, the imidazo[ 1,2-a]-(pyrrolo, thieno or furano)[3,2-d] azepine moiety will be represented by the symbol T hereinafter.

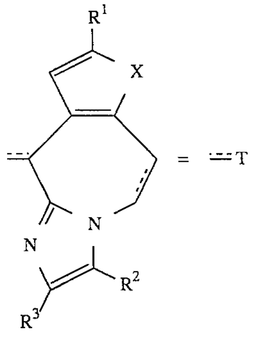

The compounds of formula (I) can be prepared by cyclizing an alcohol of formula (II) or a ketone of formula (III).

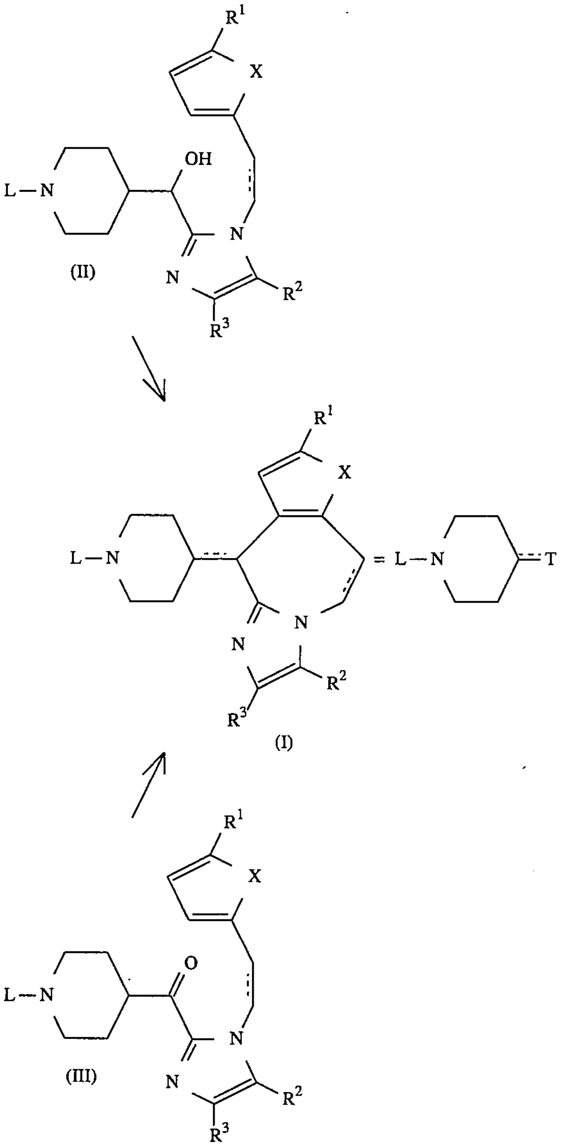

(II)

(I)

(III)

Said cyclization reaction is conveniently conducted by treating the intermediate of formula (II) or (III) with an appropriate acid, thus yielding a reactive intermediate which cyclizes to a compound of formula (I). Appropriate acids are, for example, strong acids, in particular superacid systems, e.g. methanesulfonic acid, trifluoromethanesulfonic acid, trifluoroacetic acid, methanesulfonic acid/boron trifluoride, hydrofluoric acid/boron trifluoride, or Lewis acids, e.g. aluminum chloride, trimethylsilyl iodide, phosphorylchloride and the like. Obviously, only those compounds of formula (I) wherein L is stable under the given reaction conditions can be prepared according to the above reaction procedure. In case of superacids the reaction is preferably conducted in an excess of said acid; in case of solid Lewis acids, e.g. aluminum chloride, the reaction can be conducted by fusing the starting material and the reagent, preferably in the presence of an additional salt such as sodium chloride. The cyclodehydration reaction with trimethylsilyl iodide is conveniently conducted in a reaction-inert solvent such as, for example, a halogenated hydrocarbon, e.g. trichloromethane. Particularly noteworthy is the fact that the latter reaction also can be performed on intermediates of formula (II) or (III) wherein L represents $C_{1-4}$alkyloxycarbonyl; in this case—besides cyclodehydration—also cleavage of the carbamate is observed and a compound of formula (I) wherein L is hydrogen is obtained.

In the foregoing and following preparations, the reaction mixture is worked up following art-known methods and the reaction product is isolated and, if necessary, further purified.

The compounds of formula (I) wherein the central ring of the tricyclic moiety does not contain an optional bond may also be prepared by cyclizing an intermediate of formula (IV).

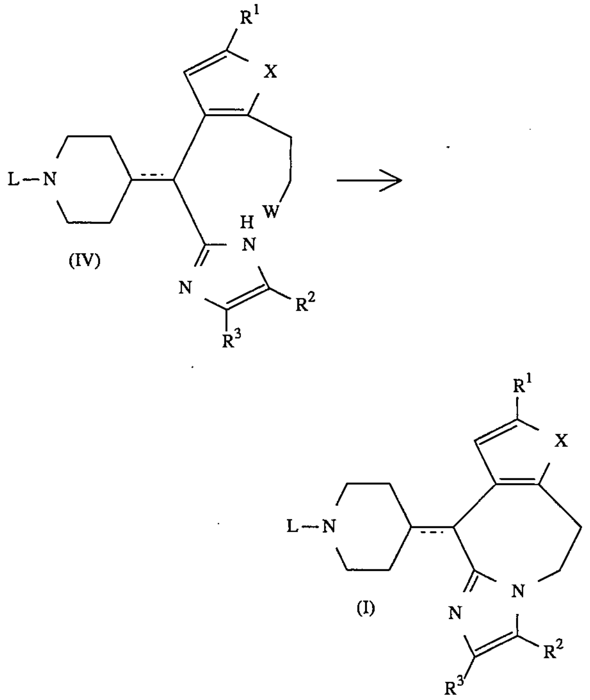

(IV)

(I)

In formula (IV) and hereinafter W represents an appropriate leaving group such as, for example, halo, e.g. chloro, bromo and the like; or a sulfonyloxy group such as, for example, methanesulfonyloxy, 4-methylbenzenesulfonyloxy and the like.

Said cyclization reaction can conveniently be conducted in a reaction-inert solvent such as, for example, an aromatic hydrocarbon, e.g., benzene, methylbenzene, dimethylbenzene and the like; an alkanol, e.g., methanol, ethanol, 1-butanol and the like; a ketone, e.g., 2-propanone, 4-methyl-2-pentanone and the like; an ether, e.g., tetrahydrofuran, 1,4-dioxane, 1,1'-oxybisethane and the like; a dipolar aprotic solvent, e.g., N,N-dimethylformamide, N,N-dimethylacetamide, dimethyl sulfoxide, nitrobenzene, 1-methyl-2-pyrrolidinone and the like; or a mixture of such solvents. The addition of an appropriate base such as, for example, an alkali or an earth alkaline metal carbonate, hydrogen carbonate, alkoxide, hydride, amide, hydroxide or oxide, e.g., sodium carbonate, sodium hydrogen carbonate, potassium carbonate, sodium methoxide, sodium ethoxide, potassium ten. butoxide, sodium hydride, sodium amide, sodium hydroxide, calcium carbonate, calcium hydroxide, calcium oxide and the like; or an organic base, such as, for example, an amine, e.g., N,N-diethylethanamine, N-(1-methylethyl)-2-propanamine, 4-ethylmorpholine, pyridine and the like may be utilized to pick up the acid which is liberated during the course of the reaction. In some instances the addition of an iodide salt, preferably an alkali metal iodide, is appropriate. Somewhat elevated temperatures and stirring may enhance the rate of the reaction.

Alternatively, the compounds of formula (I) wherein a double bond exists between the piperidinyl and the imidazo [1,2-a](pyrrolo, thieno or furano)[3,2-d]azepine moiety, said compounds being represented by formula (I-a), can be prepared by dehydrating an alcohol of formula (V) or (VI).

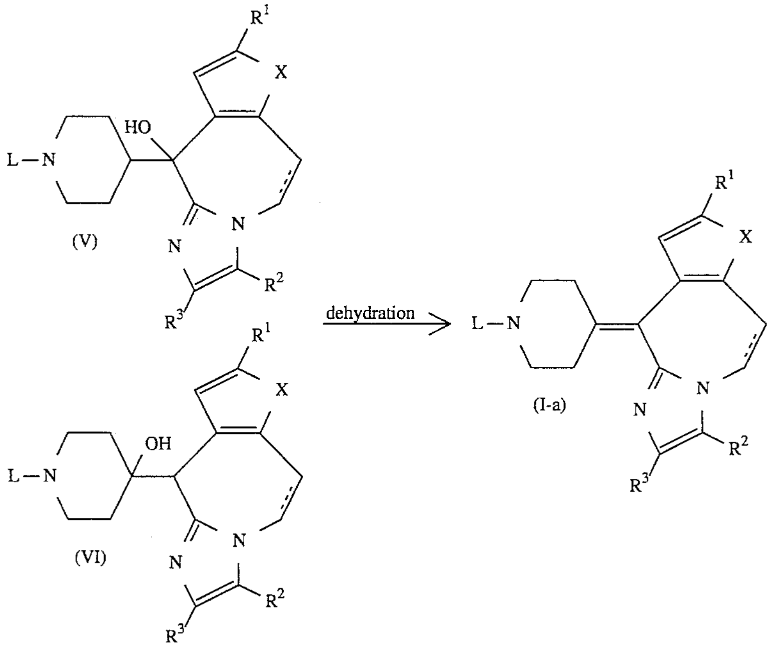

Said dehydration reaction can conveniently be conducted employing conventional dehydrating reagents following an-known methodologies. Appropriate dehydrating reagents are, for example, acids, e.g. sulfuric acid, phosphoric acid, hydrochloric acid, methanesulfonic acid, carboxylic acids, e.g. acetic acid, trifluoroacetic acid and mixtures thereof; anhydrides, e.g. acetic anhydride, phosphorus pentoxide and the like; other suitable reagents, e.g. zinc chloride, thionyl chloride, boron trifluoride etherate, phosphoryl chloride pyridine, potassium bisulfate, potassium hydroxide or phosphoryl chloride. Optionally, said dehydration reaction is conducted in a reaction-inert solvent such as, for example, a halogenated hydrocarbon, e.g. dichloromethane. In some instances said dehydration reaction may require heating the reaction mixture, more particularly up to the reflux temperature. Again, only those compounds of formula (I-a) wherein L is stable under the given reaction conditions can be prepared according to the above reaction procedure. Particularly noteworthy is the fact that the latter reaction when performed on intermediate (V) wherein the dotted line does not represent an optional bond, in some instances may also yield a compound with a double bond in the tricyclic moiety and a single bond bridging the tricyclic moiety and the piperidine:

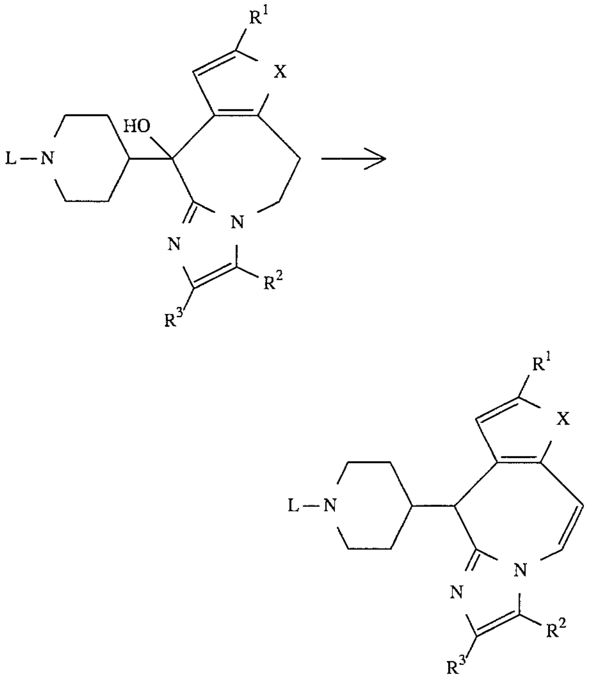

The compounds of formula (I) wherein L is $C_{1-6}$alkyl, said compounds being represented by the formula (I-b), can be convened into the compounds of formula (I) wherein L is hydrogen, said compounds being represented by the formula (I-c), in a number of manners. A first method involves dealkylating - carbonylating the compounds of formula (I-b) with a $C_{1-4}$alkylchloroformate and subsequently hydrolyzing the thus obtained compound of formula (VII-a).

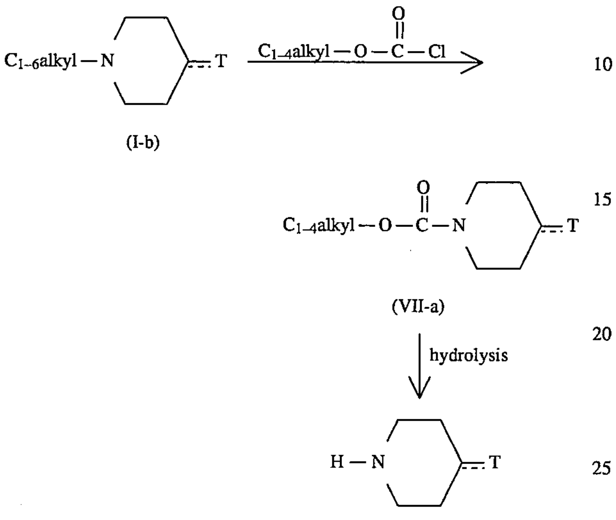

(I-b) (VII-a) (I-c)

The reaction with the $C_{1-4}$alkylchloroformate is conveniently conducted by stirring and heating the starting material (I-b) with the reagent in an appropriate solvent and in the presence of a suitable base. Appropriate solvents are, for example, aromatic hydrocarbons, e.g. methylbenzene, dimethylbenzene, chlorobenzene; ethers, e.g. 1,2-dimethoxyethane, and the like solvents. Suitable bases are, for example, alkali or earth alkaline metal carbonates, hydrogen carbonates, hydroxides, or organic bases such as, N,N-diethylethanamine, N-(1-methylethyl)-2-propanamine, and the like. The compounds of formula (VII-a) are hydrolyzed in acidic or basic media following conventional methods. For example, concentrated acids such as hydrobromic, hydrochloric acid or sulfuric acid can be used, or alternatively bases such as alkali metal or earth alkaline metal hydroxides in water, an alkanol or a mixture of water-alkanol may be used. Suitable alkanols are methanol, ethanol, 2-propanol and the like. In order to enhance the rate of the reaction it is advantageous to heat the reaction mixture, in particular up to the reflux temperature.

The compounds of formula (I-b) may also be convened directly into the compounds of formula (I-c) by stirring and heating them with an α-halo $C_{1-4}$alkyl chloroformate in an appropriate solvent such as, for example, a halogenated hydrocarbon, e.g. dichloromethane, trichloromethane; an aromatic hydrocarbon, e.g. methylbenzene, dimethylbenzene; an ether, e.g. 1,2-dimethoxyethane; an alcohol, e.g. methanol, ethanol, 2-propanol, optionally in the presence of a base such as, for example, an alkali or earth alkaline metal carbonate, hydrogen carbonate, hydroxide or an amine, e.g. N,N-diethylethanamine, N-(1-methylethyl)-2-propanamine, and the like.

The compounds of formula (I-c) can also be prepared by debenzylating a compound of formula (I-d) by catalytic hydrogenation in the presence of hydrogen and an appropriate catalyst in a reaction-inert solvent.

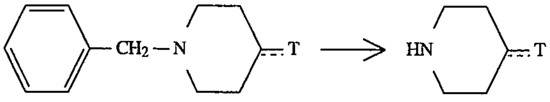

(I-d) (I-c)

A suitable catalyst in the above reaction is, for example, platinum-on-charcoal, palladium-on-charcoal, and the like. An appropriate reaction-inert solvent for said debenzylation reaction is, for example, an alcohol, e.g. methanol, ethanol, 2-propanol, and the like, an ester, e.g. ethyl acetate and the like, an acid, e.g. acetic acid and the like.

The compounds of formula (I) wherein L is other than hydrogen, said compounds being represented by formula (I-e) and said L by $L^1$, can be prepared by N-alkylating the compounds of formula (I-c) with a reagent of formula $L^1$-W (VIII).

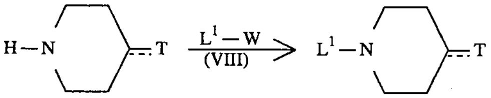

(I-c) (I-e)

Said N-alkylation reaction can conveniently be conducted in a reaction-inert solvent such as, for example, an aromatic hydrocarbon, e.g., benzene, methylbenzene, dimethylbenzene and the like; an alkanol, e.g., methanol, ethanol, 1-butanol and the like; a ketone, e.g., 2-propanone, 4-methyl-2-pentanone and the like; an ether, e.g., tetrahydrofuran, 1,4odioxane, 1,1'-oxybisethane and the like; a dipolar aprotic solvent, e.g., N,N-dimethylformamide, N,N-dimethylacetamide, dimethyl sulfoxide, nitrobenzene, 1-methyl-2-pyrrolidinone and the like; a halogenated hydrocarbon, e.g. dichloromethane, 1,2-dichloroethane and the like; or a mixture of such solvents. The addition of an appropriate base such as, for example, an alkali or an earth alkaline metal carbonate, hydrogen carbonate, alkoxide, hydride, amide, hydroxide or oxide, e.g., sodium carbonate, sodium hydrogen carbonate, potassium carbonate, sodium methoxide, sodium ethoxide, potassium ten. butoxide, sodium hydride, sodium amide, sodium hydroxide, calcium carbonate, calcium hydroxide, calcium oxide and the like; or an organic base, such as, for example, an amine, e.g., N,N-diethylethanamine, N-(1-methylethyl)-2-propanamine, 4-ethylmorpholine, pyridine and the like may be utilized to pick up the acid which is liberated during the course of the reaction. In some instances the addition of an iodide salt, preferably an alkali metal iodide, is appropriate. Somewhat elevated temperatures and stirring may enhance the rate of the reaction. Altematively, said N-alkylation may be carded out by applying an-known conditions of phase transfer catalysis reactions.

The compounds of formula (I) wherein L is $C_{1-6}$alkyl or substituted $C_{1-6}$alkyl, said L being represented by the radical $L^2H$— and said compounds by formula (I-f), can also be prepared by reductive N-alkylation of the compounds of formula (I-c) with an appropriate ketone or aldehyde of formula $L^2$=O (IX). $L^2$=O represents an intermediate of formula $L^2H_2$ wherein two geminal hydrogen atoms have been replaced by oxygen (=O) and $L^2$ is a geminal bivalent $C_{1-6}$alkylidene radical which optionally may be substituted.

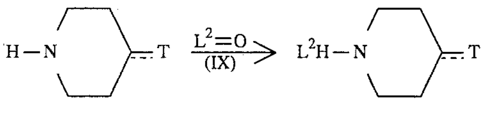

(I-c) (I-f)

Said reductive N-alkylation reaction may conveniently be carded out by reducing a mixture of the reactants in a suitable reaction-inert solvent following an-known reductive N-alkylation procedures. In particular, the reaction mixture may be stirred and/or heated in order to enhance the reaction rate. Suitable solvents are, for example, water; $C_{1-6}$alkanols, e.g. methanol, ethanol, 2-propanol and the like; esters, e.g. ethyl acetate, γ-butyrolactone and the like; ethers, e.g. 1,4-dioxane, tetrahydrofuran, 1,1'-oxybisethane, 2-methoxyethanol and the like; halogenated hydrocarbons, e.g. dichloromethane, trichloromethane and the like; dipolar aprotic solvents, e.g. N,N-dimethylformamide, dimethyl sulfoxide and the like; carboxylic acids, e.g. acetic acid, propanoic acid and the like; or a mixture of such solvents. The term "art-known reductive N-alkylation procedures" means that the reaction is carded out either with sodium cyanoborohydride, sodium borohydride, formic acid or a salt thereof, e.g. ammonium formate and the like reducing agents, or alternatively under hydrogen atmosphere, optionally at an increased temperature and/or pressure, in the presence of an appropriate catalyst such as, for example, palladium-on-charcoal, platinum-on-charcoal and the like. In order to prevent the undesired further hydrogenation of certain functional groups in the reactants and the reaction products, it may be advantageous to add an appropriate catalyst-poison to the reaction mixture, e.g., thiophene, quinoline-sulphur and the like. In some instances it may also be advantageous to add an alkali metal salt to the reaction mixture such as, for example, potassium fluoride, potassium acetate and the like salts.

The compounds of formula (I) wherein L represents a radical $Het^3$-$C_{2-4}$alkyl, said compounds being represented by formula (I-g), can be prepared by the addition reaction of a compound of formula (I-c) to an appropriate alkene of formula (X).

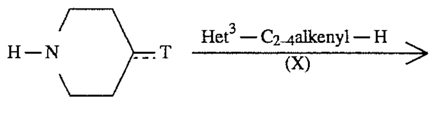

(I-c)

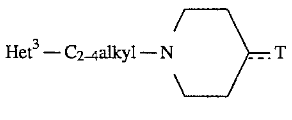

(I-g)

The compounds of formula (I) wherein L is 2-hydroxy-$C_{2-6}$alkyl or aryloxy-2-hydroxy-C $_{2-6}$alkyl, said compounds being represented by formula (I-h), can be prepared by reacting a compound of formula (I-c) with an epoxide (XI) wherein $R^6$ represents hydrogen, $C_{1-4}$ alkyl or aryloxy $C_{1-4}$alkyl.

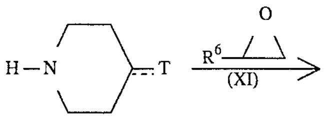

(I-c)

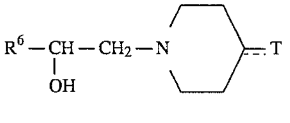

(I-h)

The reaction of (I-c) with respectively (X) or (XI) can be conducted by stirring and, if desired, heating the reactants in a reaction-inert solvent such as, for example, a ketone, e.g. 2-propanone, 4-methyl-2-pentanone; an ether, e.g. tetrahydrofuran; an alcohol, e.g. methanol, ethanol, 1-butanol; a dipolar aprotic solvent, e.g. N,N-dimethylformamide and the like.

The compounds of formula (VII-b) can be prepared from a compound of formula (I) wherein L represents P—NH—$C_{2-4}$alkyl, said compounds being represented by formula (I-i), wherein P is a protective group, such as, for example, $C_{1-4}$alkyloxycarbonyl, following an-known deprotection methods.

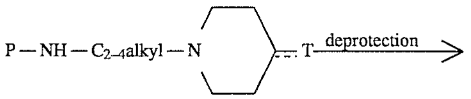

(I-i)

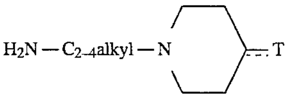

(VII-b)

The compounds of formula (VII-b) can also be prepared by reducing a compound of formula (VII-c).

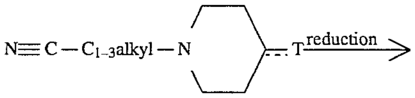

(VII-c)

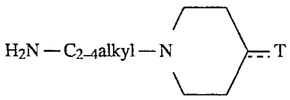

(VII-b)

Said reduction can be conducted by stirring and, if desired, heating the starting material in a hydrogen containing medium in the presence of a catalyst, e.g. palladium-on-charcoal, platinum-on-charcoal, Raney Nickel and the like, in a suitable solvent, e.g. methanol, ethanol and the like, or by reduction with a metal hydride, e.g. lithium aluminum hydride in an ether, e.g. tetrahydrofuran.

The compounds of formula (I) wherein L is a radical of formula —Alk—Y—$Het^1$, said compounds being represented by formula (I-j), can be prepared by alkylating a compound of formula (I-k) with a reagent of formula (XII).

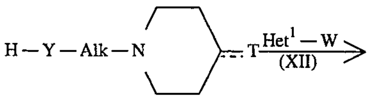

(I-k)

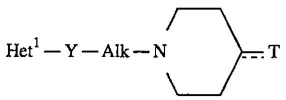

(I-j)

Alternatively, the compounds of formula (I-j) can also be prepared by reacting a compound of formula (VII-d) with a reagent of formula (XIII).

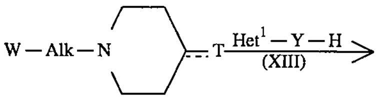

(VII-d)

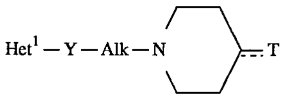

(I-j)

The above alkylation reactions may conveniently be conducted in a reaction-inert solvent, e.g. methylbenzene, dimethylbenzene, 2-propanone, 4-methyl-2-pentanone, 1,4-dioxane, tetrahydrofuran, N,N-dimethylformamide, N,N-dimethylacetamide, methanol, ethanol, 1-butanol and the like. The addition of an appropriate base, e.g. an alkali metal or earth alkaline metal carbonate or hydrogen carbonate, sodium hydride, N,N-diethylethanamine or N-(1-methylethyl)-2-propanamine may be used to pick up the acid liberated during the course of the reaction. In order to enhance the rate of the reaction the reaction mixture may be heated.

The compounds of formula (I) wherein L represents a radical of formula —Alk—NH—CO—Het$^2$, said compounds being represented by formula (I-1) can be prepared by N-acylating a compound of formula (VII-b) with a carboxylic acid of formula (XIV) or a reactive functional derivative thereof.

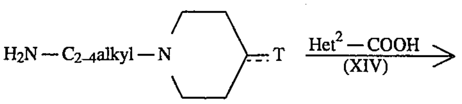

(VII-b)

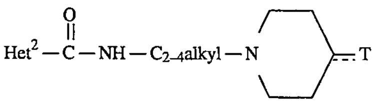

(I-l)

The reaction of (XIV) with (VII-b) may generally be conducted following art-known acylation reaction procedures. For example, the carboxylic acid may be convened into a reactive derivative, e.g. an an hydride or a carboxylic acid halide, which subsequently is reacted with (VII-b); or by reacting (XIV) and (VII-b) with a suitable reagent capable of forming amides, e.g., N,N-methanetetraylbis [cyclohexamine], 2-chloro-1-methyl-pyridinium iodide and the like. Said reactions are conveniently conducted in a suitable solvent such as, for example, an ether, e.g., tetrahydrofuran, a halogenated hydrocarbon, e.g., dichloromethane, trichloromethane, a dipolar aprotic solvent and the like. The addition of a base such as, for example, N,N-diethylethanamine and the like may be appropriate.

The compounds of formula (I) wherein L represents $C_{1-4}$alkylamino(thio)carbonyl-amino $C_{2-4}$alkyl, said compounds being represented by the formula (I-m), can be prepared from the compounds of formula (VII-b) by reaction with a $C_{1-4}$alkyliso(thio)cyanate in a reaction-inert solvent such as, for example, an ether, e.g. tetrahydrofuran.

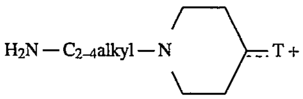

(VII-b)

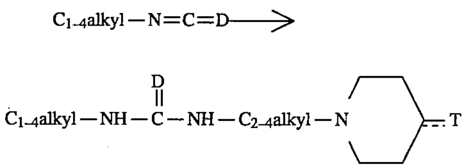

D = S:(I-m-1)
D = O:(I-m-2)

The compounds of formula (I) wherein Het$^1$ represents an imidazo[4,5-c]pyridin-2-yl radical and Y represents NH, said compounds being represented by formula (I-n) can be prepared from a compound of formula (VII-b) according to the following reaction scheme.

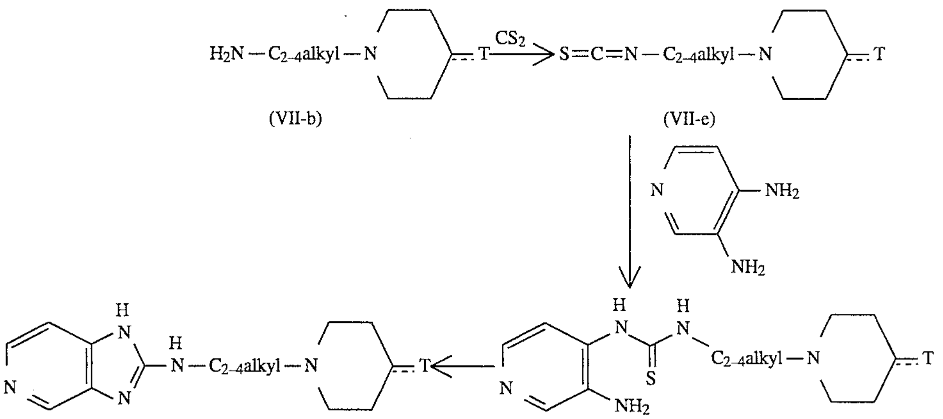

(VII-b) (VII-e)

(I-n) (VII-f)

The isocyanate (VII-e) is prepared by reacting (VII-b) with carbon disulfide in the presence of a dehydrating reagent such as N,N-methanetetraylbis[cyclohexanamine] in a reaction-inert solvent such as an ether, e.g. tetrahydrofuran. The isothiocyanate is reacted with 3,4-diaminopyridine in a reaction-inert solvent such as an ether, e.g. tetrahydrofuran, and the resulting thiourea is cyclized by treatment with an appropriate metal oxide such as mercury(II)oxide. In certain instances it may be appropriate to supplement the reaction mixture with a small amount of sulfur.

The compound (VII-e) or the corresponding isocyanate can also be employed to prepare compounds of formula (I-m), by reacting (VII-e) or the corresponding isocyanate with a $C_{1-4}$alkylamine in a reaction-inert solvent such as an ether, e.g. tetrahydrofuran.

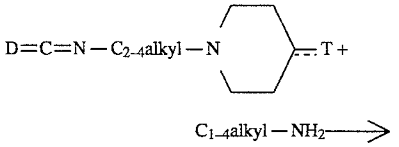

-continued

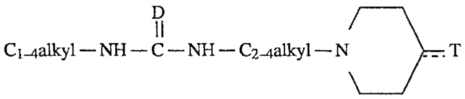

D is S:(I-m-1)
D is O:(I-m-2)

The compounds of formula (I) wherein Het[1] represents 1-methyl-2-imidazolyl and Y represents NH, said compounds being represented by formula (I-o) can be prepared from the compounds of formula (VII-b) according to the following reaction scheme.

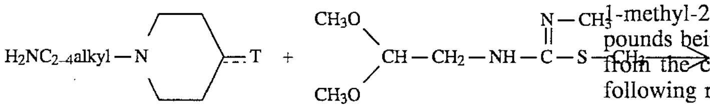

(VII-b) (XV)

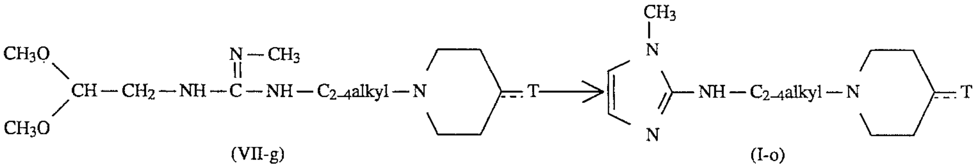

(VII-g) (I-o)

The compound (VII-b) is reacted with a reagent of formula (XV) in a reaction-inert solvent such as an alcohol, e.g. 2-propanol, and the thus obtained intermediate (VII-g) is cyclized by treatment with an acidic aqueous solution, such as a hydrochloric acid aqueous solution.

The compounds of formula (I) wherein Het[3] represents a 2—$C_{1-4}$alkyloxycarbonyl-1-pyrrolyl radical, said compounds being represented by the formula (I-p), can be prepared by reacting a compound of formula (VII-b) with a reagent of formula (XVI).

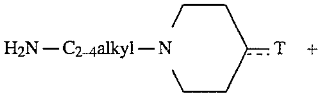

(VII-b)

-continued

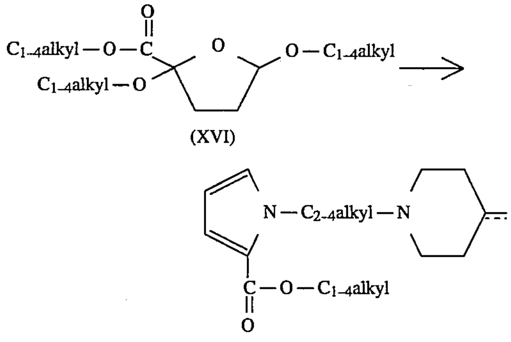

(XVI)

(I-p)

The above reaction preferably is conducted in the presence of an acid, such as, for example, acetic acid. The compound of formula (I-p) optionally may be hydrolyzed to the corresponding hydroxycarbonyl compound in the presence of an acid or base.

The compounds of formula (I) wherein $R^5$ is C1-6alkyl or $C_{1-4}$alkylcarbonyl, said compounds being represented by the formula (I-q), and said $R^5$ by $R^{5-a}$, can be prepared by reacting a compound of formula (I) wherein $R^5$ is hydrogen, said compound being represented by the formula (Ior), with a reagent of formula (XVII).

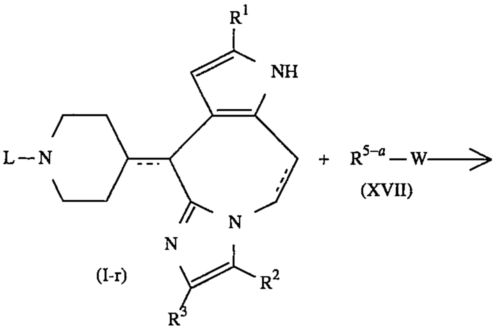

(I-r)

(XVII)

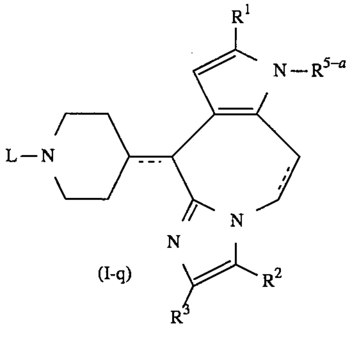

(I-q)

The above reaction can conveniently be conducted in a reaction-inert solvent and in the presence of a base, as described hereinbefore for the preparation of the compounds of formula (I-e) from the compounds of formula (I-c) and for the compounds of formula (I-1) from the intemediates of formula (VII-b).

The compounds of formula (I) wherein $R^1$ is halo, said compounds being represented by the formula (I-s), can be prepared by reacting a compound of formula (I) wherein $R^1$ is hydrogen, said compound being represented by the formula (I-t), with an appropriate halogenating reagent in a reaction-inert solvent.

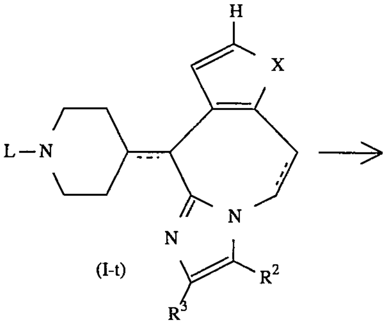

(I-t)

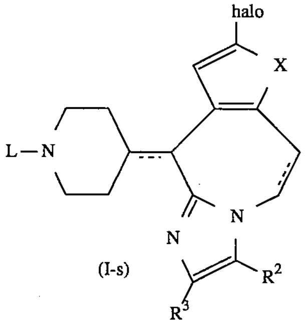

(I-s)

A suitable halogenating reagent in the above reaction is, for example, an N-halogentated amide, e.g. N-bromosuccinimide, a dihalogenide, e.g. chlorine, bromine, in the presence of a catalyst, e.g. iron; a hypohalous acid, e.g. hypochlorous acid and the like. A suitable reaction-inert solvent for said halogenation reaction is, for example, a dipolar aprotic solvent, e.g. N,N-dimethylformamide, N,N-dimethylacetamide, and the like.

The compounds of formula (I) wherein R 1 is formyl, said compounds being represented by the formula (I-u), can be prepared by formylating a compound of formula I-t).

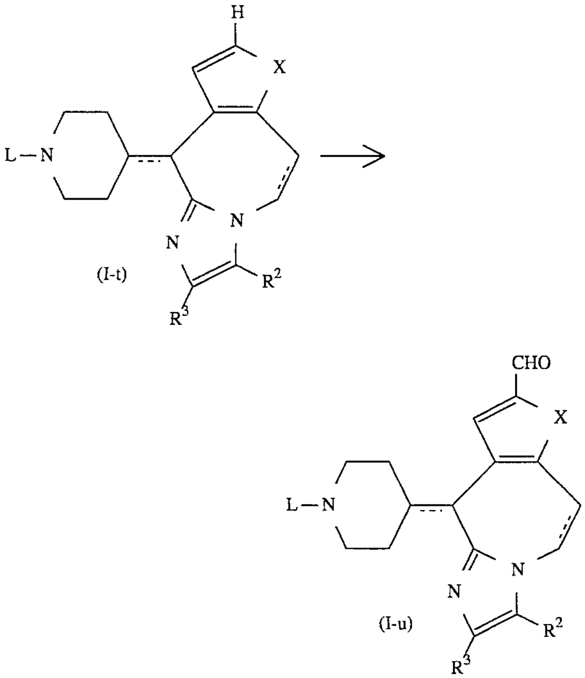

(I-t) (I-u)

Said formylation can conveniently be conducted in the presence of a formylating reagent such as, for example, phosphoryl chloride and a formamide, e.g. N,N-dimethylformamide (Vilsmeyer-Haack), zinc cyanide and hydrochloric acid (Gatterman), trichloromethane and hydroxide ions (Reimer-Tiemann), and the like.

The compounds of formula (I) wherein $R^1$ is hydroxymethyl, said compounds being represented by the formula (I-v), can be prepared from the reduction of a compound of formula (I-u) in a reaction-inert solvent.

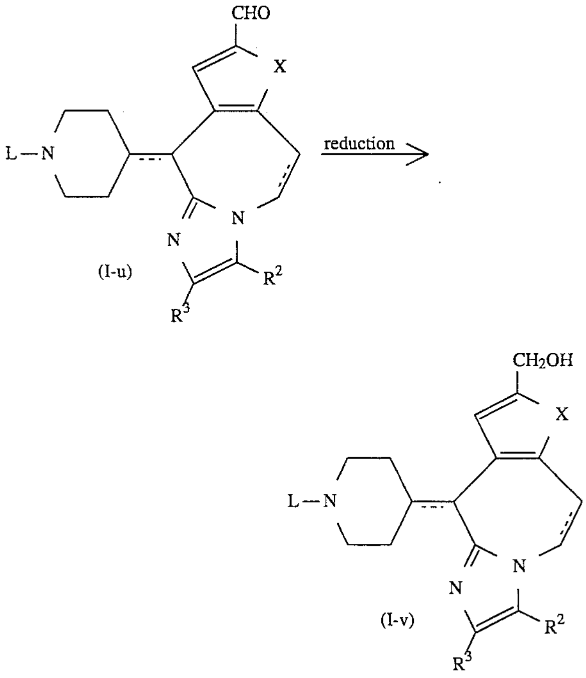

(I-u) (I-v)

Suitable reducing reagents are, for example, metallic hydrides, e.g. lithium aluminum hydride, sodium borohydride, sodium cyanoborohydride, and the like. An appropriate reaction-inert solvent for the above reduction reaction is, for example, an alcohol, e.g. methanol, ethanol, 2-propanol and the like.

The compounds of formula (I) wherein $R^1$ is hydroxycarbonyl, said compounds being represented by the formula (I-w), can be prepared from the oxidation of a compound of formula (I-u).

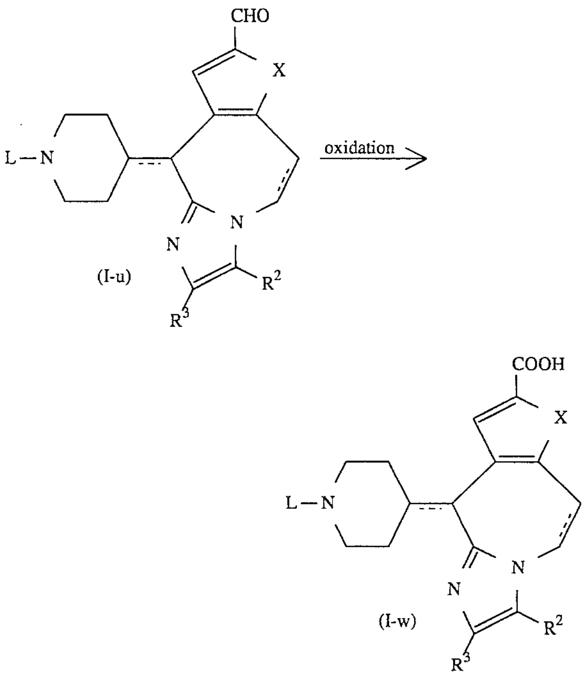

(I-u) (I-w)

A suitable oxidizing reagent is, for example, permanganate, chromic acid, silver oxide, silver nitrate, optionally in the presence of a base, e.g. potassium hydroxide, and the like.

The compounds of formula (I) wherein $R^1$ is $C_{1-4}$alkyloxycarbonylethenyl, said compounds being represented by the formula (I-x), can be prepared by reacting a compound of formula (I-u) with a reagent of formula (XVIII) in the presence of a base, e.g. pyridine, pipeddine and the like.

(I-u) + $HOOC-CH_2-COOC_{1-4}$alkyl ⟶
(XVIII)

-continued

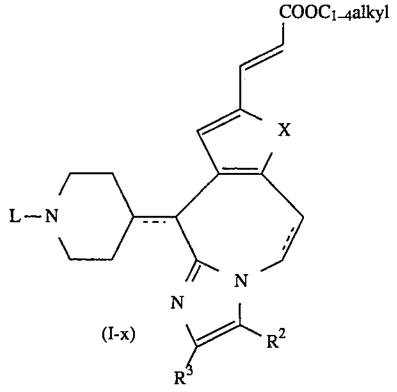

(I-x)

The compounds of formula (I-x) can be further hydrolyzed into a compound of formula (I) wherein $R^1$ is hydroxycarbonylethenyl, in the presence of an acid or a base.

The compounds of formula (I) may further be converted into each other following art-known functional group transformation procedures.

For example, the compounds of formula (I) wherein L contains a $C_{1-4}$ alkyloxy-carbonyl moiety can be hydrolyzed to a compound of formula (I) wherein L contains a hydroxycarbonyl moiety, in the presence of an acid or a base.

The compounds of formula (I) wherein L is cyanophenyl $C_{1-6}$alkyl can be converted into a compound of formula (I) wherein L is aminocarbonylphenyl $C_{1-6}$alkyl upon treatment with an acid, such as for example, acetic acid, sulfuric acid, and the like, in an aqueous environment.

The compounds of formula (VII-a to VII-g) intervening in the preparations described hereinbefore are novel and have especially been developed for use as intermediates in said preparations. Consequently, the present invention also relates to novel compounds of formula

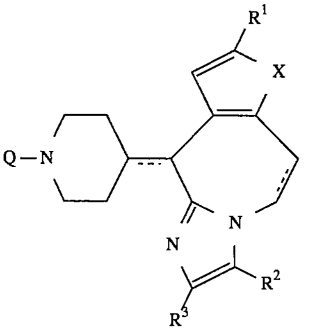

(VII)

a pharmaceutically acceptable addition salt or a stereochemically isomeric form thereof, wherein X, $R^1$, $R^2$ and $R^3$ are as defined for the compounds of formula (I); and Q represents ($C_{1-6}$alkyl or phenyl)oxycarbonyl, $C_{1-4}$alkylcarbonyl or $C_{1-6}$alkyl substituted with halo, cyano, amino, isothiocyanato, (4-amino- 3-pyridinyl)aminothiocarbonylamino, $(CH_3O)_2CH—CH_2—NH—C(=NCH_3)—NH$, or methylsulfonyloxy.

Particularly interesting compounds of formula (VII) are those wherein Q represents ($C_{1-6}$alkyl or phenyl)oxycarbonyl, $C_{1-4}$alkylcarbonyl or $C_{1-6}$ alkyl substituted with cyano or amino, the pharmaceutically acceptable acid addition salts and the stereochemically isomeric forms thereof.

In the following paragraphs there are described several methods of preparing the starting materials employed in the foregoing preparations.

The intermediates of formula (II) can be prepared from the corresponding ketones of formula (III) by reduction.

$$(III) \xrightarrow{\text{reduction}} (II)$$

Said reduction can conveniently be conducted by reacting the starting ketone (III) with hydrogen in a solvent such as, for example, an alcohol, e.g. methanol, ethanol; an acid, e.g. acetic acid; an ester, e.g. ethyl acetate; in the presence of a hydrogenation catalyst, e.g. palladium-on-charcoal, platinum-on-charcoal, Raney Nickel.

In order to enhance the rate of the reaction, the reaction mixture may be heated and, if desired, the pressure of the hydrogen gas may be raised.

Alternatively, the alcohols of formula (II) can also be prepared by reducing the ketones (III) with a reducing agent such as, for example, lithium aluminum hydride, sodium borohydride, sodium cyanoborohydride and the like in a suitable solvent such as, for example, an ether, e.g. 1,1'-oxybisethane, tetrahydrofuran and the like; an alcohol, e.g. methanol, ethanol and the like.

The ketones of formula (III) wherein the dotted line is not an optional bond can be prepared by N-alkylating an intermediate of formula (XIX) with a reagent of formula (XXI) wherein W represents a reactive leaving group as defined hereinbefore.

Said N-alkylation reaction can conveniently be conducted following the procedures employed in preparing the compounds of formula (I-e) from the compounds of formula (I-c).

The ketones of formula (III) can be prepared by the addition of a compound of formula (XIX) to a reagent of formula (XX) under the reaction conditions described hereinbefore for the preparation of the compounds of formula (I-g) from the compounds of formula (I-c).

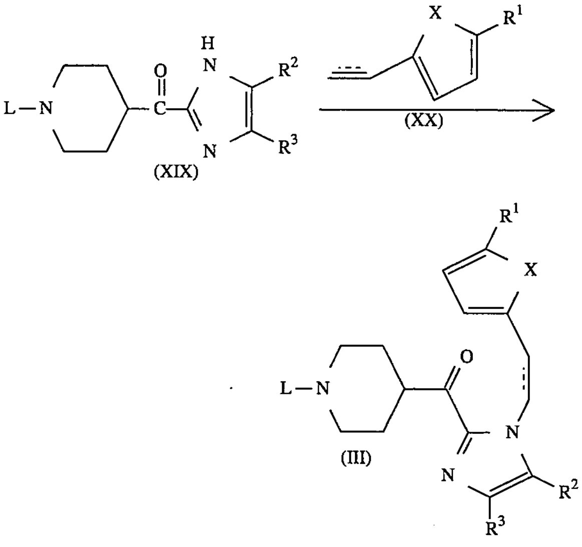

(XIX) (XX) (III)

-continued

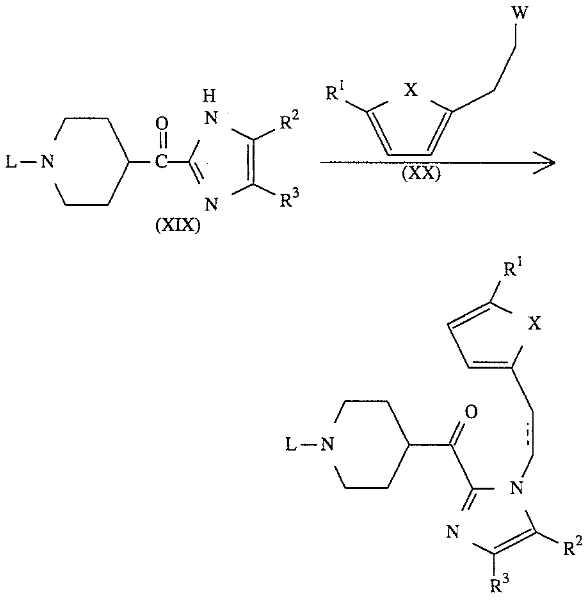

(XIX)

(XX)

Further, the ketones of formula (III) wherein the dotted line is not an optional bond, may also be prepared by reductive N-alkylation of the compounds of formula (XIX), under the reaction conditions described for the preparation of the compounds of formula (I-f) from the compounds of formula (I-c).

The intermediates of formula (XIX) are conveniently prepared from reacting an ester of formula (XXII) with a protected imidazole derivative of formula (XXIII) in the presence of a strong base such as, for example, methyl lithium, butyl lithium, sodium amide, a dialkyl lithium amide, e.g. diisopropyl lithium amide, or a mixture thereof, in a reaction-inert solvent, e.g. tetrahydrofuran, hexane, methylbenzene and the like, or a mixture thereof.

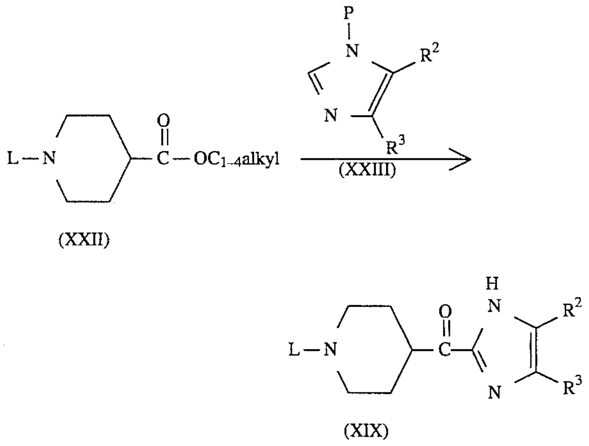

(XXII)

(XXIII)

(XIX)

In (XXIII) P represents a protective group such as, for example, di($C_{1-4}$alkoxy)-methyl, $C_{1-4}$alkoxymethyl, benzenesulfonyl, trimethylsilylethoxymethyl, N,N-dialkyl-aminomethyl which can be removed by acid hydrolysis. The reaction of (XXII) and (XXIII) is conveniently conducted at low temperatures. For example, the reagent (XXIII) may be added at a temperature between about −80° C. to about −40° C. to the strong base. Subsequently, the ester (XXII) is added and the reaction mixture is allowed to warm up gently to room temperature. The thus obtained product is converted into intermediate (XIX) by very mild acid hydrolysis and isolated in a conventional manner.

The ketones of formula (III) wherein L represents methyl, can be prepared from the ketones wherein L represents hydrogen by reductive N-alkylation with formaldehyde following the methods described hereinbefore for the preparation of the compounds of formula (I-f) from the compounds of formula (1-c).

The ketones of formula (III) wherein L represents hydrogen are prepared by hydrolysis of a carbamate of formula (III-a) in acidic or basic media following conventional methods as described hereinbefore for the preparation of compounds of formula (I-c) from the compounds of formula (I-b).

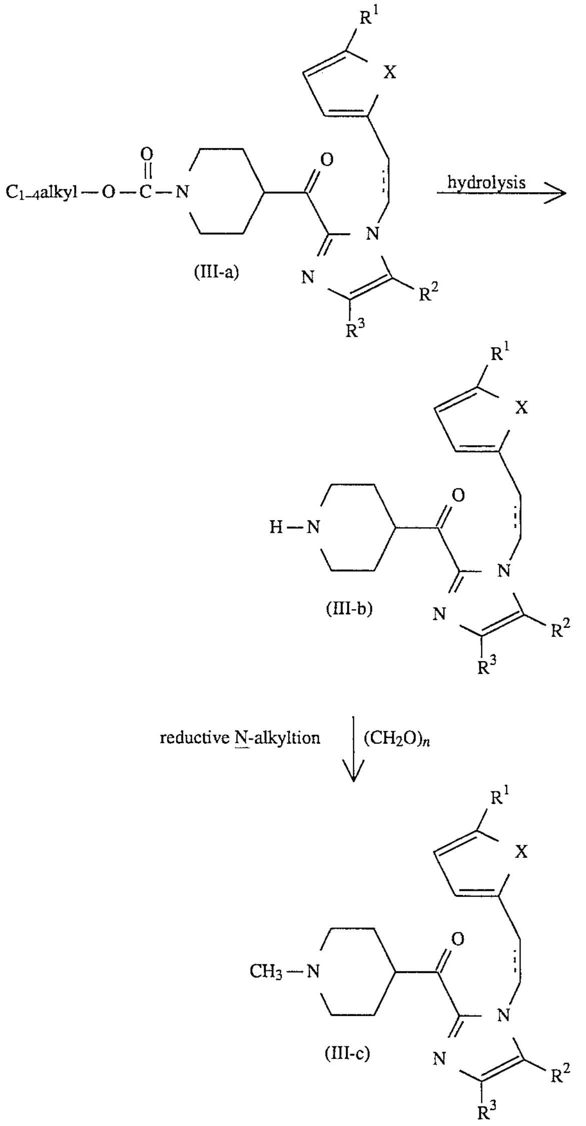

(III-a)

(III-b)

(III-c)

The intermediates of formula (Ill-a) can be prepared by reacting an acid halide of formula (XXIV) with an imidazole derivative of formula (XXV).

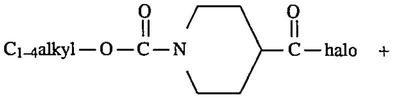

(XXIV)

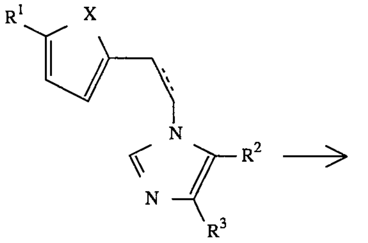

(III-a)

(XXV)

Said reaction is conveniently conducted by stirring and heating the reactants in the presence of a base such as, for example, an amine, e.g. N,N-diethylethanamine, N-methylmorpholine and the like, in a suitable solvent such as, for example, pyridine, acetonitrile or a mixture thereof.

The intermediates of formula (III-c) can also be prepared from an ester of formula (XXVI) by reaction with an imidazole of formula (XXV) in the presence of a strong base such as, for example, methyl lithium, butyl lithium, sodium amide, a dialkyl lithium amide, e.g. diisopropyl lithium amide, or a mixture thereof, in a suitable reaction-inert solvent, e.g. tetrahydrofuran, hexane, methylbenzene and the like, or a mixture thereof.

Said reaction is conveniently conducted at low temperatures. For example the reagent (XXV) may be stirred at a temperature between about −80° C. to about −40° C., whereupon the strong base is added. Subsequently the ester is added and the reaction mixture is allowed to warm up gently to room temperature.

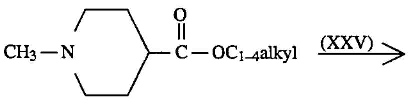

(III-c)

(XXVI)

The intermediates of formula (V) can be prepared by addition of a Grignard reagent (XXVII) to a ketone of formula (XXVIII) in a reaction-inert solvent, e.g. tetrahydrofuran.

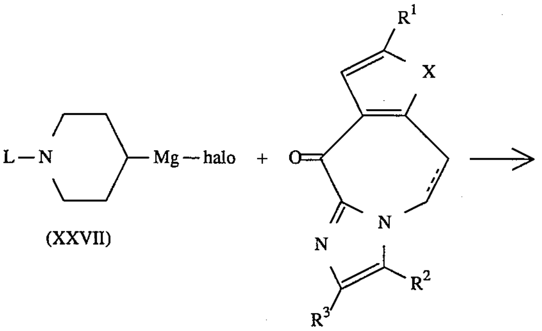

(XXVII) (XXVIII)

-continued

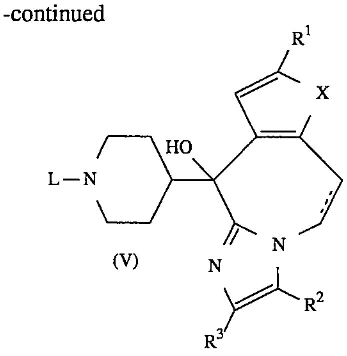

(V)

The tricyclic ketones of formula (XXVIII) in turn are prepared from intermediates of formula (XXIX) by oxidation with a suitable oxidizing reagent in a reaction-inert solvent.

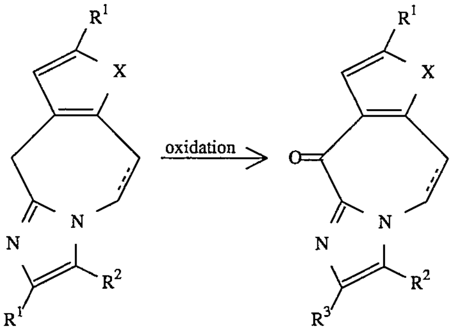

(XXIX) (XXVIII)

Suitable oxidizing reagents are, for example, manganese dioxide, selenium dioxide, ceric ammonium nitrate and the like. Reaction-inert solvents are, for example, halogenated hydrocarbons, e.g. dichloromethane, trichloromethane and the like.

The compounds of formula (XXIX) wherein the dotted lines do not represent an optional bond can be prepared from the corresponding compounds of formula (XXIX) wherein said dotted lines do represent an optional bond, following art-known hydrogenation procedures, e.g. by reaction with hydrogen in the presence of a hydrogenation catalyst.

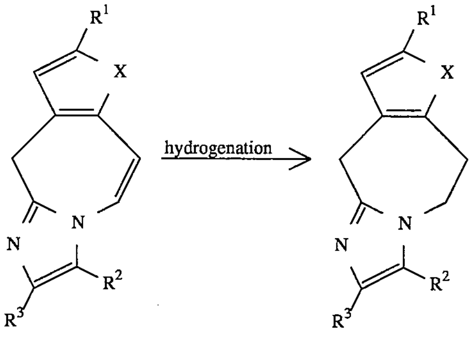

(XXIX-a) (XXIX-b)

The intermediates of formula (XXIX-a) can be prepared from a benzazepine of formula (XXX) by reaction with a reagent of formula (XXXI) and cyclization of the thus obtained intermediate (XXXII) in an acidic medium. In (XXXI) R represents $C_{1-4}$alkyl or both radicals R taken together represent $C_{2-6}$alkanediyl, e.g. 1,2-ethanediyl, 1,3-propanediyl, 2,2-dimethyl-1,3-propanediyl.

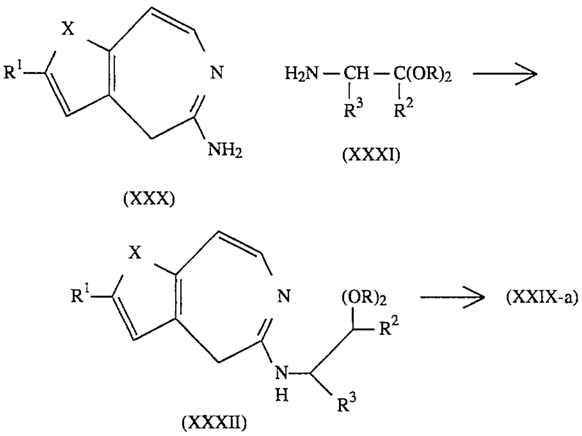

(XXX) (XXXI) (XXXII) (XXIX-a)

The preparation of (XXXII) is conveniently conducted by stirring and heating the reactants in a reaction-inert solvent such as, for example, an alcohol, e.g. methanol, ethanol and the like.

The cyclization reaction to the intermediates of formula (XXIX-a) is conducted by stirring and heating the starting material (XXXII) in a carboxylic acid such as, for example, acetic acid, propanoic acid, optionally in admixture with a mineral acid such as, for example, hydrochloric acid.

The intermediates of formula (XXIX) can also be prepared from cyclization of an intermediate of formula (XXXIII).

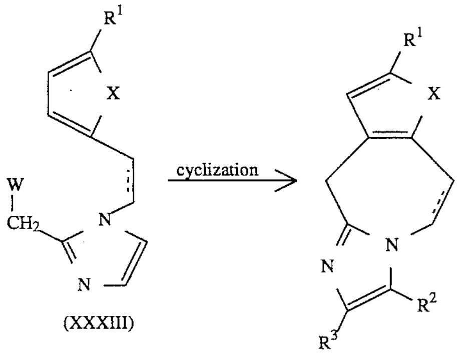

(XXXIII) (XXIX)

Said cyclization reaction is conveniently conducted in the presence of a Lewis acid, e.g. aluminum chloride, and the like. In some instances it may be appropriate to supplement the reaction mixture with a suitable amount of sodium chloride.

The intermediates of formula (V) can also be prepared from the cyclization of an intermediate of formula (III) in the presence of an acid in a reaction-inert solvent.

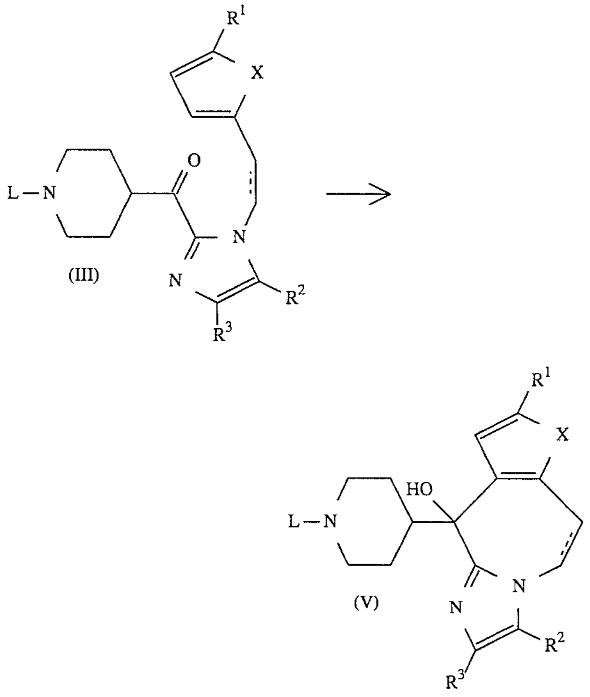

(III) (V)

An appropriate acid in the above reaction is, for example, a Lewis acid, e.g. tin(IV)chloride and the like. A suitable reaction-inert solvent is, for example, a halogenated hydrocarbon, e.g. dichloromethane, 1,2-dichloroethane, and the like.

The intermediates of formula (VI) can be prepared by reaction of a ketone of formula (XXXIV) with an intermediate of formula (XXIX) in the presence of e.g. lithium diisopropyl amide in a reaction-inert solvent, e.g. tetrahydrofuran.

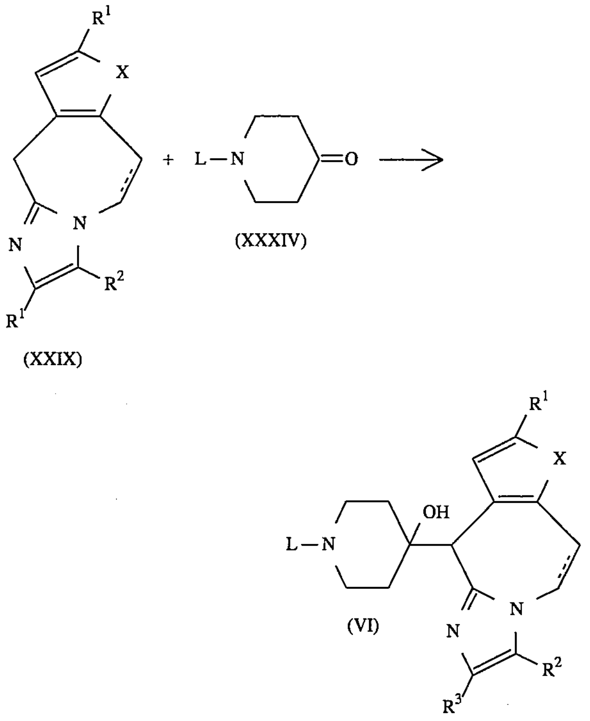

(XXIX) (XXXIV) (VI)

The intermediates of formula (VII-c) can be prepared by N-alkylating a compound of formula (I-c) with a reagent of formula (XXXV) following the procedures described hereinbefore for the preparation of the compounds of formula (I-e).

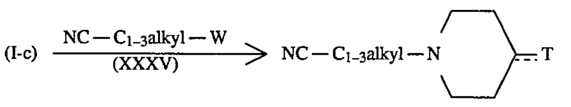

(VII-c)

The intermediates of formula (VII-d) can be prepared from the compounds of formula (I-k) wherein Y is oxygen by reaction with a halogenating reagent such as, for example, thionyl chloride, phosphorous trichloride, phosphoryl chloride and the like, or by reaction with a sulfonating reagent such as, for example, methanesulfonyl chloride, 4-methylbenzenesulfonyl chloride and the like.

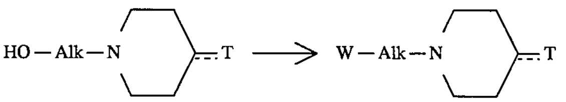

(I-k-1) (VII-d)

The intermediates of formula (XV) can be prepared by the following reaction sequence.

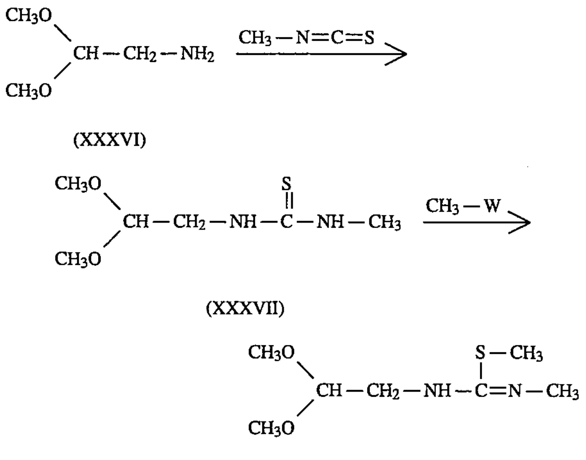

(XXXVI) (XXXVII) (XV)

The reaction of (XXXVI) with the isothiocyanate reagent can conveniently be conducted in a reaction-inert solvent such as, for example, an ether, e.g. tetrahydrofuran and the like. The resulting intermediate of formula (XXXVII) is methylated in a reaction-inert solvent such as, for example, a ketone, e.g. 2-propanone and the like.

The compounds of formula (XXIX) intervening in the preparations described hereinbefore are novel and have especially been developed for use as intermediates in said preparations. Consequently, the present invention also relates to novel compounds of formula

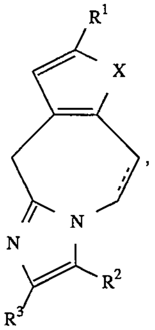

(XXIX)

the addition salt forms thereof and the stereochemically isomeric forms thereof, wherein $R^1$, $R^2$, $R^3$ and X are as defined under formula (I).

The compounds of formula (I) and some of the compounds of formula (VII), in particular those wherein Q represents ($C_{1-6}$ alkyl or phenyl)oxycarbonyl, $C_{1-4}$alkylcarbonyl or $C_{1-6}$ alkyl substituted with cyano or amino, the pharmaceutically acceptable acid addition salts and the stereochemically isomeric forms thereof, possess useful pharmacological properties. In particular they are active antiallergic agents, which activity can clearly be demonstrated by the test results obtained in a number of indicative tests.

Antihistaminic activity can be demonstrated in 'Protection of Rats from Compound 48/80—induced Lethality' test (Arch. Int. Pharmacodyn. Ther., 234, 164–176, 1978); 'Histamine—induced Lethality in Guinea Pigs' test (Arch. Int. Pharmacodyn. Ther., 251, 39–51, 1981); and the broad antiallergic activity can be demonstrated in 'Passive cutaneous anaphylaxis in Rats' test (Drug Dev. Res., 5, 137–145, 1985) (For some compounds this test has been modified by replacing compound 48/80 by Ascaris allergens) and the 'Ascaris Allergy in Dogs' test (Arch. Int. Pharmacodyn. Ther., 251, 39–51, 1981 and Drug Dev. Res., 8, 95–102, 1986).

The compounds of the present invention show a broad spectrum antiallergic profile as is evidenced by the results obtained in the diversity of test procedures cited hereinbefore.

A second advantageous feature of the compounds of the present invention resides in their excellent oral activity; the present compounds when administered orally have been found to be practically equipotent with the same being administered subcutaneously.

A particularly important asset of most of the present compounds is their lack of sedating properties at therapeutic dose levels, a troublesome side effect associated with many antihistaminic and antiallergic compounds. The non-sedating properties of the present compounds can be demonstrated, for example, by the results obtained in studying the sleep— wakefulness cycle of the rat (Psychopharmacology, 97,436–442, (1989)).

Another interesting feature of the present compounds relates to their fast onset of action and the favorable duration of their action.

In view of their antiallergic properties, the compounds of formula (I) and the compounds of formula (VII) wherein Q represents ($C_{1-6}$alkyl or phenyl)oxycarbonyl, $C_{1-4}$ alkylcarbonyl or $C_{1-6}$alkyl substituted with cyano or amino, and their acid addition salts are very useful in the treatment of a broad range of allergic diseases such as, for example, allergic rhinitis, allergic conjunctivitis, chronic urticaria, allergic asthma and the like.

In view of their useful antiallergic properties the subject compounds may be formulated into various pharmaceutical forms for administration purposes. To prepare the antiallergic compositions of this invention, an effective amount of the particular compound, in base or acid addition salt form, as the active ingredient is combined in intimate admixture with a pharmaceutically acceptable carder, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the cartier will usually comprise sterile water, at least in large part, though other ingredients, for example to aid solubility, may be included. Injectable solutions, for example, may be prepared in which the carder comprises saline solution, glucose solution or a mixture of saline and glucose solution. Injectable suspensions may also be prepared in which case appropriate liquid carders, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on or as an ointment. Acid addition salts of the subject compounds due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carder. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention also relates to a method of treating warm-blooded animals suffering from said allergic diseases by administering to said warm-blooded animals an effective antiallergic amount of a compound of formula (I) or a compound of formula (VII) wherein Q represents ($C_{1-6}$alkyl or phenyl)oxycarbonyl, $C_{1-4}$alkylcarbonyl or $C_{1-6}$alkyl substituted with cyano or amino, or a pharmaceutically acceptable acid addition salt form thereof.

In general it is contemplated that an effective antiallergic amount would be from about 0.001 mg/kg to about 20 mg/kg body weight, and more preferably from about 0.01 mg/kg to about 5 mg/kg body weight.

The following examples are intended to illustrate and not to limit the scope of the present invention in all its aspects.

EXPERIMENTAL PART

A. Preparation of the Intermediates

EXAMPLE 1 a) A mixture of 17.8 g of [2-(1-methyl-1H-pyrrol-2-yl)ethyl] methanesulfonate (ester), 11.7 g of 1H-imidazole, 14 g of potassium carbonate and 410 ml of tetrahydrofuran was stirred for 3 days at reflux temperature. After cooling, the reaction mixture was evaporated and the residue was taken up in water. The product was extracted with dichloromethane and the extract was dried, filtered and evaporated. The residue was purified by column chromatography (silica gel; $CH_2C1_2/CH_3OH$ 95:5). The eluent of the desired fraction was evaporated and the residue was co-evaporated with methylbenzene (3×). The product was filtered off and dried, yielding 9.3 g (61.7%) of 1-[2-(1-methyl- 1H-pyrrol-2-yl)ethyl]-1H-imidazole (interm. 1);

b) To a stirred and cooled (−70° C.) mixture of 5.5 g of 1-methyl N-(1-methylethyl)ethanamine and 100 ml of tetrahydrofuran under nitrogen atmosphere, there were added dropwise 15.0 g of a solution of n. butyllithium in hexanes 2.5M. After stirring for 15 min. at −40° C., there were added dropwise 8.76 g of intermediate (1) at −70° C. and after 1 hour 9.4 g of ethyl 1-methyl-4-piperidi.necarboxylate. The whole was stirred first for 1 hour at −70° C. and then for 2 hours at room temperature, diluted with water and evaporated. The residue was taken up in water and the product was extracted with dichloromethane. The extract was dried, filtered and evaporated and the residue was purified by column chromatography (silica gel; $CH_2Cl_2/CH_3OH$ 95:5→80:20). The eluent of the desired fraction was evaporated, yielding 9 g (60.0%) of (1-methyl-4piperidinyl)[ 1-[2-(1-methyl-1H-pyrrol-2-yl)ethyl]-1H-imidazol-2-yl]methanone (interm. 2).

EXAMPLE 2 a) To a stirred and cooled (ice-bath) mixture of 49 g of 1-methyl-1H-pyrrole-2-ethanol, 47.6 g of N,N-diethylethanamine and 500 ml of dichloromethane, there were added portionwise 34 ml of methanesulfonyl chloride. Stirring was continued overnight at room temperature. The reaction mixture was diluted with water and the product was extracted with dichloromethane. The extract was dried, filtered and evaporated, yielding 85.5 g (100%)of 1-methyl-1H-pyrrole-2-ethanol methanesulfonate (ester) (interm. 3);

b) To a stirred mixture of 1.3 ml of a dispersion of sodium hydride in mineral oil (50%) and 150 ml of N,N-dimethylformamide under nitrogen atmosphere, there were added portionwise 1.65 g of 4-methyl-1H-imidazole and, after stirring for 1 hour at room temperature, dropwise a solution of 5.1 g of intermediate (3) in some N,N-dimethylformamide. Stirring at room temperature was continued for 4 hours. The reaction mixture was poured into ice-water and the product was extracted with dichloromethane. The extract was dried, filtered and evaporated and the residue was converted into the (E)-2-butenedioate (1:1) salt in ethanol. The salt was recrystallized from ethanol (2×), yielding 2 g (32.7%) of 4-methyl-1-[2-(1-methyl-1H-pyrrol-2-yl)ethyl]-1H-imidazole (E)-2-butenedioate (1:1); mp. 137.3° C. (interm. 4);

c) To a stirred and cooled (−70° C.) mixture of 17.2 g of 1-methyl-N-(1-methylethyl)ethanamine and 300 ml of tetrahydrofuran under nitrogen atmosphere there were added portionwise 42.2 g of a solution of n.butyllithium in hexanes 2.5M. After stirring for 15 min. at −40° C., there was added dropwise at −70° C. a solution of 23.5 g of intermediate (4) in 100 ml of tetrahydrofuran. Stirring was continued for 1 hour at room temperature and then there was added a solution of 23.3 g of ethyl 1-methyl-4-pipefidinecarboxylate in 100 ml of tetrahydrofuran at −70° C. After stirring for 1 hour at −70° C. and overnight at room temperature, the reaction mixture was diluted with water and evaporated. The residue was taken up in water and the product was extracted with dichloromethane. The extract was dried, filtered and evaporated. The residue was purified by column chromatography (silica gel; $CH_2Cl_2/CH_3OH(NH_3)$ 97:3). The eluent of the desired fraction was evaporated, yielding 32.2 g (82.6%) of[4-methyl-1-[2-(1-methyl-1H-pyrrol- 2-yl)ethyl] -1H-imidazol-2-yl](1-methyl-4-pipefidinyl)methanone; mp. 80.6° C. (interm. 5);

d) To a stirred mixture of 26 ml of a dispersion of sodium hydride in mineral oil (50%) in 100 mi of N,N-dimethylformamide under nitrogen atmosphere there were added portionwise 31 g of 4-methyl-1H-imidazole and, after 1 hour, dropwise a solution of 99.6 g of intermediate (3) in 100 ml of N,N-dimethylformamide. Stirring was continued for 4 hours and then the reaction mixture was poured into ice-water. The product was extracted with dichloromethane and the extract was dried, filtered and evaporated. The residue was converted into the (E)-2-butenedioate (1:1) salt in ethanol. The salt was crystallized twice from ethanol * and then taken up in water. After basifying with $K_2CO_3$, the product was extracted with dichloromethane. The extract was dried, filtered, treated with activated charcoal, filtered again and evaporated, yielding 29.6 g (41.2% ) of 4-methyl-1-[2-(1-methyl-1H-pyrrol-2-yl)ethyl]-1H-imidazole. The combined mother liquors * were evaporated and the residue was treated similarly as the precipitate hereinbefore. The residue was further purified by column chromatography (silica gel; $CH_2Cl_2/CH_3OH$ 97:3). The eluent of the desired fraction was evaporated and the residue was converted into the ethanedioate (1:1) salt in 2-propanone. The salt was taken up in water and further treated similarly as hereinbefore, yielding 16.4 g (22.8%) of 5-methyl-1-[2-(1-methyl-1H-pyrrol-2-yl)ethyl]-1H-imidazole (interm. 6);

e) To a stirred and cooled (−70° C.) mixture of 12 g of 1-methyl-N-(1-methylethyl)ethanamine and 350 ml of tetrahydrofuran under nitrogen atmosphere, there were added portionwise 29.2 g of a solution of n.butyllithium in hexanes 2.5M. After stirring for 15 min. at −40° C., there was added dropwise a solution of 16.4 g of intermediate (6) in some tetrahydrofuran at −70° C. Stirring at −70° C. was continued for 1 hour and then there was added dropwise a solution of 16.4 g of ethyl 1-methyl-4-piperidinecarboxylate in some tetrahydrofuran. The whole was stirred for 1 hour at −70° C. and overnight at room temperature, diluted with water and evaporated. The residue was partitioned between water and dichloromethane. The aqueous layer was separated and re-extracted with dichloromethane. The combined organic layers were dried, filtered and evaporated. The residue was purified by column chromatography (silica gel; $CH_2Cl_2/CH_3OH(NH_3)$ 97:3→95:5). The eluent of the desired fraction was evaporated, yielding 18 g (65.8%) of[5-methyl-l-[2-(1-methyl-1H-pyrrol-2-yl)ethyl]-lH-imidazol-2-yl] (1-methyl-4piperidinyl)methanone (interm. 7).

EXAMPLE 3

To a stirred and cooled (ice-bath) mixture of 9.3 g of intermediate (1), 19 g of N,N-diethylethanamine and 150 ml of acetonitfile there were added dropwise 34.8 g of ethyl 4-chlorocarbonyl-1-piperidinecarboxylate, keeping the temperature below 20° C. After stirring for 2 hours at room temperature and for 4 hours at reflux temperature, there were added portionwise 16 ml of NaOH 50%. Stirring was continued for ½ hour at reflux temperature. The reaction mixture was evaporated and the residue was taken up in water. The product was extracted with dichloromethane and the extract was dried, filtered and evaporated. The product was filtered off and dried, yielding 25 g (100%) of ethyl 4-[[1-[2-(1-methyl-1H-pyrrol-2-yl)ethyl]-1H-imidazol-2-yl]carbonyl]- 1- piperidinecarboxylate (interm. 8).

EXAMPLE 4 a) To a stirred and cooled (0° C.) mixture of 13 g of 2-thiopheneethanol and 15.3 g of N,N-diethylethanamine in 90 ml of dichloromethane there were added dropwise 8.6 ml of methanesulfonyl chloride. Stirring was continued for ½ hour and then the reaction mixture was washed with ice-water, dried, filtered and evaporated. The residue was taken up in 2,2'-oxybispropane and the whole was evaporated again, yielding 20 g (95.7%) of 2-thiopheneethanol methanesulfonate (ester) (interm. 9);

In a similar manner were also prepared:

1H-pyrrole-2-ethanol methanesulfonate (ester) (interm. 10); and 5-methyl-2-furanethanol methanesulfonate (ester) (interm. 11);

b) To a stirred and cooled (−70° C.) mixture of 132 g of (1-methylethyl)-2-propanamine in 3540 ml of tetrahydrofuran under nitrogen atmosphere were added portionwise 340 g of a solution of n. butyllithium in hexanes 2.5M. After stirring for 15 minutes at −40° C., the mixture was cooled to −70° C. and 170 g of 1-(1,1-diethoxymethyl)-1H-imidazole were added dropwise. The reaction mixture was stirred for 1 hour at this temperature and 283 g of 1,1-dimethylethyl 4-(ethyloxycarbonyl)-1-piperidinecarboxylate were added dropwise. The reaction mixture was stirred first for 1 hour at −70° C. and then for 18 hours at room temperature. The mixture was decomposed with 50 ml of water, then acidified with hydrochloric acid (pH 4–5) at <10° C., then stirred for 15 minutes at 10° C. and treated with potassium carbonate. The reaction mixture was evaporated, the residue was taken up in water and the product was extracted with dichloromethane. The extract was dried, filtered and evaporated. The residue was purified by column chromatography (silica gel; $CH_2Cl_2/CH_3CN$ 85:15). The eluent of the desired fraction was evaporated, yielding, after crystallization with acetonitrile, 182 g (65%) of 1,1-dimethylethyl 4-[ (1H-imidazol-2-yl)carbonyl]-1-piperidinecarboxylate; mp. 148.3° C. (interm. 12);

In a similar manner was also prepared:
 (1H-imidazol-2-yl)(1-methyl-4-piperidinyl)methanone; mp. 143.6° C. (interm. 13);

c) To a stirred mixture of 4.3 g of a dispersion of sodium hydride in mineral oil (50%) and 200 ml of N,N-dimethylformamide under nitrogen atmosphere were added 19.5 g of intermediate (12). After stirring for 1 hour at room temperature, the reaction mixture was heated to 60° C. and a solution of 14.4 g of intermediate (9) in N,N-dimethylformamide was added dropwise. After stirring overnight at 60° C., the reaction mixture was decomposed with water and the product was extracted with 4-methyl-2-pentanone. The extract was dried, filtered and evaporated. The residue was purified by column chromatography (silica gel; $CH_2Cl_2/CH_3OH$ 95:5). The eluent of the desired fraction was evaporated, yielding 15.7 g (57.5%) of 1,1-dimethylethyl 4-[[1-[2-(2-thienyl)-ethyl-] 1H-imidazol-2-yl]carbonyl]-1-piperidinecarboxylate (interm. 14);

In a similar manner were also prepared:
 (1-methyl-4-piperidinyl)[1-[2-(1H-pyrrol-2-yl)ethyl]-1H-imidazol-2-yl]methanone (interm. 15);
 [1-[2-(2-furanyl)ethyl]-1H-imidazol-2-yl](1-methyl-4-piperidinyl)methanone (interm. 16); and
 [1-[2-(5-methyl-2-furanyl)ethyl]-1H-imidazol-2-yl](1-methyl-4-piperidinyl] methanone (interm. 17).

d) A mixture of 8.5 g of intermediate (14), 25 ml 2-propanol/HCl and 150 ml of methanol was stirred for 15 minutes at reflux temperature. After cooling, the precipitated product was filtered off and dried, yielding 7 g (89%) of (4-piperidinyl) [ 1-[ 2-(2-thienyl)ethyl]-1H-imidazol-2-yl] methanone dihydrochloride; mp. 236.4° C. (interm. 18);

e) A mixture of 18.1 g of intermediate (18), 5 g of polyoxymethylene, 15 g of potassium acetate, 2 ml of thiophene, 150 ml of methanol was hydrogenated in the presence of 3 g of palladium-on-charcoal catalyst 10%. After hydrogenation, the catalyst was filtered off and the flitrate was evaporated. The residue was taken up in water, dichloromethane and ammonium hydroxyde. After stirring for 15 minutes, the separated aqueous layer was re-extracted with dichloromethane. The combined dichloromethane layers were dried, filtered and evaporated, yielding 15.1 g (100%) of (1-methyl-4-piperidinyl)[ 1-[2-(2-thienyl)ethyl]-1H-imidazol-2-yl]methanone (interm. 19).

EXAMPLE 5 a) Through 50 ml of ethanol on an ice-bath was bubbled an excess of hydrochloric acid gas. Then there were added 23.3 g of 3-thiopheneacetonitrile and stirring was continued for 1 hour on ice-bath. The mixture was put overnight in a refrigerator and then evaporated at 40° C. with 2,2'-oxybispropane. The residue was stirred in 1,1'-oxybisethane and the precipitate was filtered off and dried at room temperature, yielding 28.8 g (73.6%) of O-ethyl 3-thiopheneethanimidate hydrochloride (interm. 20);

b) To a solution of 28.8 g of intermediate (20) in 150 ml of 1,2-dimethoxyethane at 15° C. were added portionwise 14.7 g of 2,2odimethoxyethanamine. The whole was stirred overnight and the mixture was evaporated, yielding 37.1 g (100%) of N-(2,2-dimethoxyethyl) 3-thiopheneethanimidamide monohydrochloride (interm. 21);

c) A mixture of 37.1 g of intermediate (21) in 150 ml of acetic acid was stirred under a nitrogen atmosphere. Then there were added portionwise 27 g of methanesulfonic acid and the whole was stirred overnight. The mixture was poured into ice and basified with sodium hydroxide. The precipitate was filtered off and the water layer was extracted with a mixture of dichloromethane and methanol. The organic layer was separated, dried, filtered and evaporated. The precipitate and the residue were put together, yielding 13.8 g (60%) of 4H-thieno[2,3-d]azepin-5-amine (interre. 22); d) A mixture of 12.35 g of intermediate (22) and 15.9 g of 2,2-dimethoxyethanamine in 100 ml of methanol was stirred overnight at reflux temperature. The reaction mixture was evaporated, yielding 18.9 g (100%) of N-(2,2-dimethoxyethyl)-4H-thieno[2,3-d]-azepin- 5-amine (interre. 23);

e) A mixture of 18.9 g of intermediate (23) in 260 ml of acetic acid and 35 ml of hydrochloric acid was stirred for 16 hours at 70° C. The reaction mixture was evaporated and the residue was taken up in water. The whole was basified with sodium hydroxide and the product was extracted with dichloromethane. The extract was separated, dried, filtered and evaporated. The residue was purified by column chromatography (silica gel; $CH_2Cl_2/CH_3OH(NH_3)$ 95:5). The eluent of the desired fraction was evaporated and the residue was dried, yielding 4.6 g (13%) of 10H-imidazo[ 1,2-a]thieno[3,2-d]azepine (interm. 24);

f) A mixture of 4.6 g of intermediate (24) and 23 g of manganese dioxide in 250 ml of trichloromethane was stirred for 48 hours at reflux temperature. The mixture was filtered over diatomaceous earth while hot and the flitrate was evaporated. The residue was crystallized from acetonitrile, filtered off and dried, yielding 2.55 g (51.6%) of 10H-imidazo[ 1,2-a]thieno[ 3,2-d]azepin-10-one; mp. 267.0° C (interm. 25);

g) To a mixture of a few crystals of iodine, 1.5 g of magnesium turnings and 10 ml of tetrahydrofuran under a nitrogen atmosphere were added 1.2 ml of bromoethane. The whole was heated till reflux temperature and a solution of 8 g of 4-chloro-1-methyl-piperidine in 30 ml of tetrahydrofuran was added dropwise. After refluxing for 1 hour there were added portionwise 30 ml of tetrahydrofuran and 10.1 g of intermediate (25) and refluxing was continued for 30 minutes. After cooling, there was added $NH_4Cl$ (aq.) and the product was extracted with trichloromethane. The extract was separated, dried, filtered and evaporated and the residue was purified by column chromatography (silica gel; $CH_2Cl_2/CH_3OH$ 95:5→$CH_2Cl_2/CH_3OH(NH_3)$ 90:10). The eluent of the desired fraction was evaporated and the residue was dried, yielding 9.9 g (65.5%) of (+)-10-(1-methyl-4- piperidinyl )-10H-imidazo[ 1,2-a]thieno[ 3,2-d]azepin-10-ol (interm. 26).

EXAMPLE 6 a) A mixture of 34 g of (1 H-imidazol-2-yl)(4-piperidinyl)methanone dihydrobromide, 20 g of benzaldehyde and 15 g of potassium acetate in 500 ml of methanol and 1 ml of a solution of thiophene in methanol (4%) was hydrogenated at normal pressure and at 50° C. in the presence of 3 g of palladium-on-charcoal catalyst 10%. After the calculated amount of hydrogen was taken up, the catalyst was filtered off and the flitrate was evaporated. The residue was partitioned between dichloromethane and $NH_4Cl$ (aq.). The aqueous layer was extracted with dichloromethane and the combined organic layers were dried, filtered and evaporated. The residue was taken up in water, acidified with hydrochloric acid and washed twice with 2,2'-oxybispropane. The aqueous layer was basified with NaOH 50% and extracted three times with dichloromethane. The combined organic layers were dried, filtered and evaporated. The residue was stirred in 2,2'-oxybispropane, filtered off and dried, yielding 22.3 g (83%) of (1H-imidazol-2-yl)-[ 1-(phenylmethyl)-4-piperidinyl]methanone; mp. 121.0° C. (interm. 27);

b) To a stirred mixture of 24 g of sodium hydride 50% and 1300 ml of N,N-dimethylformamide under a nitrogen atmosphere were added portionwise 130 g of intermediate (27) and stirring was continued for 1.5 hours. Then there was added dropwise a solution of 113 g of 2-thiopheneethanol methanesulfonate (ester) in 200 ml of N,N-dimethylformamide. After stirring overnight at 60° C., the mixture was decomposed with ice and evaporated. The residue was taken up in dichloromethane and washed with water. The organic layer was dried, filtered and evaporated. The residue was taken up in water, acidified with hydrochloric acid and washed twice with 2,2'-oxybispropane. The aqueous layer was basified with NaOH 50% and extracted three times with dichloromethane. The organic layer was dried, filtered and evaporated, yielding 190 g (100%) of [1-(phenyl methyl )-4-piperidinyl][1-[2-(2-thienyl)ethyl]-1H-imidazol-2-yl] methanone (interm. 28);

In a similar manner was also prepared: [1-[2-(1-methyl-1H-pyrrol-2-yl)ethyl]-1H-imidazol-2-yl][1-(phenylmethyl)-4 -piperidinyl]methanone (interm. 29);

c) To a stirred solution of 40 g of intermediate (28) in 250 ml of 1,2-dichloroethane under a nitrogen atmosphere were added dropwise 50 ml of tin(IV)chloride. After refluxing for 5 hours, the mixture was cooled on an ice-ethanol bath. The reaction mixture was decomposed with ice and basified with NaOH 50%. The product was extracted three times with dichloromethane. The organic layer was washed with water, dried, filtered and evaporated. The residue was purified by column chromatography (silica gel; $CH_2Cl_2/CH_3OH(NH3)$ 98:2). The eluent of the desired fraction was evaporated and the residue was stirred in 2,2'-oxybispropane, yielding 20.8 g (54.8%) of (±)-6,10-dihydro- 10-[ 1-(phenylmethyl)-4-piperidinyl]-5H-imidazo[1,2-a]thieno[3,2-d]azepin-10-ol; mp. 189.0° C. (interm. 30);

In a similar manner were also prepared:

(±)-6, 10-dihydro-10-(1-methyl-4-piperidinyl)-5H-imidazo[1,2-a]thieno[3,2-d]azepin-10ol; mp. 160.0° C. (interm. 31);

(±)-6, 10-dihydro-8-methyl-10-(1-methyl-4-piperidinyl)-5H-furo[3,2-d]imidazo[ 1,2-a]azepin-10-ol; mp. 206.4° C. (interm. 32);

(±)-6, 10-dihydro-10-(1-methyl-4-piperidinyl)-5H-furo [3,2-d]imidazo[1,2-a]azepin- 10 ol; mp. 190.3° C. (interm. 33).

EXAMPLE 7 a) A mixture of 4.2 g of 2,2-dimethoxyethanamine, 3.6 g of isothiocyanatomethane and 100 ml of tetrahydrofuran was stirred overnight. The reaction mixture was evaporated, yielding 7.1 g (99%) of N-(2,2-dimethoxyethyl)-N'-methylthiourea as an oily residue (interm. 34);

b) A mixture of 7.1 g of intermediate (34), 8.5 g of iodomethane and 100 ml of 2-propanone was stirred overnight. The reaction mixture was evaporated, yielding 12.8 g (99%) of methyl N-(2,2-dimethoxyethyl)-N'-methylcarbamimidothioate monohydroiodide (interm. 35).

EXAMPLE 8

2.3 g of methyl 4'-methyl-(1, 1'-biphenyl)-2-carboxylate was dissolved in 900 ml of tetrachloromethane under a nitrogen flow. Then there were added 17.8 g of 1-bromo-2,5-pyrrolidinedione and a catalytic amount of dibenzoyl peroxide. After stirring for 2.5 hours at reflux temperature under a nitrogen atmosphere, the reaction mixture was cooled and filtered. The flitrate was evaporated, yielding >30 g (100% ) of methyl 4'-(bromomethyl)[ 1,1'-biphenyl]-2-carboxylate as a crude residue (interm. 36).

B. Preparation of the Final Compounds

EXAMPLE 9

A mixture of 8 g of intermediate (2) and 40 ml methanesulfonic acid was stirred for 6 hours at 80° C. After cooling, the reaction mixture was poured into ice water. The whole was treated with sodium hydroxide and extracted with dichloromethane. The extract was dried, filtered and evaporated. The residue was purified by column chromatography (silica gel; $CH_2Cl_2/CH_3OH$ 95:5→$CH_2Cl_2/CH_3OH(NH_3)$ 90:10). The eluent of the desired fraction was evaporated and the residue was stirred in 1,1'-oxybisethane. The precipitated product was filtered off and recrystallized from 4-methyl-2pentanone, yielding 0.81 g (10.8%) of 6,10-dihydro-7-methyl-10-(1-methyl-4-piperidinylidene)-5H,7H-imidazo[1,2-a]pyrrolo[3,2-dlazepine; mp. 186.8° C. (comp. 2). mp. 190.3° C. (interm. 33).

EXAMPLE 10

To a stirred and cooled (0° C.) mixture of 20 g of intermediate (8) and 200 ml of trichloromethane under nitrogen atmosphere were added dropwise 30 ml of trimethylsilyl iodide. The reaction mixture was stirred for 1 hour at room temperature and then refluxed overnight. After cooling to 0° C., 200 ml of methanol were added dropwise. The whole was evaporated, the residue was taken up in water and treated with potassium carbonate. The product was extracted with dichloromethane. The extract was dried, filtered and evaporated. The residue was purified by column chromatography (silica gel; $CH_2Cl_2/CH_3OH/NH_3$ 90:10). The eluent of the desired fraction was evaporated, the residue was taken up in 2-propanone and treated with activated charcoal. The precipitate was filtered off and the flitrate was evaporated. The residue was boiled in ethyl acetate. After cooling, the precipitated product was filtered off (fraction 1) and the flitrate was evaporated (fraction 2). The combined fractions were converted into the (E)-2- butenedioate salt in ethanol, yielding 6.7 g (31.9%) of 5,6,7,10-tetrahydro-7-methyl-10-(4-piperidinylidene)imidazo[ 1,2-a]pyrrolo[3,2-d]azepine (E)-2-butenedioate (1:2); mp. 206.0° C. (comp. 1).

EXAMPLE 11

50 ml of trifluoromethylsulfonic acid were added to 2.5 g of intermediate (19) cooled in an ice bath and under nitrogen atmosphere. The reaction mixture was stirred for 7 days at room temperature and then for 18 hours at 35° C. After pouring into crushed ice, the whole was treated with sodium hydroxide and the product was extracted with dichloromethane. The extract was dried, filtered and evaporated. The residue was purified by column chromatography (silica gel; $CH_2Cl_2/CH_3OH$ /NH3OH:$NH_3$ 95:0:5→93:0:7 and $CH_2Cl_2/CH_3OH/CH_3OH:NH_3$ 90:10:1→90:10:2). The eluent of the desired fraction was evaporated. The residue was convened into the (E)-2-butenedioate salt in ethanol. The salt was filtered off and recrystallized from ethanol, yielding 0.63 g (19.1%) of 5,6-dihydro-10-(1-methyl-4-piperidinylidene)-10H-imidazo[1,2-a]thieno[ 3,2-d]azepine (E)-2-butenedioate(1:1); mp.227.2° C. (comp. 6).

EXAMPLE 12

A mixture of 6 g of intermediate (2) and 100 ml of 2,2,2-trifluoroacetic acid was stirred for 1.5 hours at reflux temperature. After cooling, the reaction mixture was poured into ice-water and basified with sodium hydroxide. The product was extracted with dichloromethane and the extract was separated, dried, filtered and evaporated. The residue was purified by column chromatography (silica gel; $CH_2Cl_2$/ $CH_3OH/CH_3OH(NH_3)$ 96:0:4→90:10:2). The eluent of the desired fraction was evaporated and the residue was purified by column chromatography (amino; $CH_2Cl_2/CH_3OH$ 98:2). The eluent of the desired fraction was evaporated and the residue was crystallized from 2,2'-oxybispropane, yielding 0.4 g (7%) of (±)-7,10-dihydro-7-methylo10-(1-methyl-4-piperidinyl)imidazo[1,2-a]pyrrolo[ 3,2-d]azepine; mp. 143.1 ° C. (comp. 18).

EXAMPLE 13

To a stirred mixture of 30 g of intermediate (30) and 450 ml of dichloromethane at 0° C. under a nitrogen atmosphere was added dropwise a solution of 11 g of thionyl chloride in 50 ml of dichloromethane. After stirring overnight at room temperature, the reaction mixture was cooled till 0° C. and there was added dropwise 50 ml of a solution of ammonia in methanol (7N). The whole was stirred for 1 hour and there were added 100 ml of ice water. After stirring strongly, the organic layer was separated, dried, filtered and evaporated. The residue was purified by column chromatography (silica gel; $CH_2Cl_2/CH_3OH$ 95:5). The eluent of the desired fraction was evaporated and the residue was recrystallized from a mixture of acetonitrile and 2,2'-oxybispropane, yielding 5.1 g (17.6% ) of 6,10-dihydro-10-[1-(phenylmethyl)-4-piperidinylidene]-5H-imidazo[ 1,2-a]thieno[3,2-d]azepine; mp. 177.7° C. (comp. 77).

EXAMPLE 14

To a mixture of 9.9 g of intermediate (26) and 150 ml of phosphoryl chloride at reflux temperature were added carefully a few drops of water. After stirring for 2 hours at reflux temperature, the reaction mixture was evaporated. The residue was taken up in water and basified with sodium hydroxide. The product was extracted with dichloromethane and the extract was separated, dried, filtered and evaporated. The residue was purified by column chromatography (silica gel; $CH_2Cl_2/CH_3OH$ 95:5→$CH_2Cl_2$/CH $_3OH(NH_3)$ 95:5). The eluent of the desired fraction was evaporated and the residue was crystallized from acetonitrile, yielding 4.15 g (44%) of 10o(1-methyl-4-piperidinylidene)- 10H-imidazo[1,2-althieno[3,2-d]azepine; mp. 136.4° C. (comp. 9).

EXAMPLE 15

A mixture of 12.1 g of intermediate (31) and 100 ml of phosphoryl chloride was stirred for 8 hours at reflux temperature. The reaction mixture was evaporated and the residue was poured into ice water and basified with sodium hydroxide. The product was extracted with dichlorometh ane and the extract was dried, filtered and evaporated. The residue was purified by column chromatography (silica gel; $CH_2Cl_2/CH_3OH$/CH $_3OH(NH_3)$ 90:10:1). The eluent of the desired fraction was evaporated and the residue was converted into the hydrochloride salt (1:2) in 2-propanol, yielding 2.1 g (14% ) of (±)-10-(1-methyl-4-piperidinyl )-10H-imidazo[1,2-a]thieno[3,2-d]azepine dihydrochloride monohydrate; mp. 240.9° C. (comp. 41).

EXAMPLE 16 a) A mixture of 17 g of compound (9), 25.2 g of ethylchloroformate, 750 ml of methylbenzene and 18 g of N,N-diethylethanamine was stirred for 3 hours at reflux temperature. The mixture was evaporated and the residue was taken up in water and basified with sodium hydroxide 50%. The product was extracted twice with dichloromethane and the extract was dried, filtered and evaporated. Again 25.2 g of ethyl chloroformate and a solution of 12 g of N,N-diethylethanamine in 500 ml of methyl-benzene were added and stirring at reflux temperature was continued for 3 hours. The mixture was evaporated and the residue was taken up in water and basified with sodium hydroxide 50%. The product was extracted three times with dichloromethane. The combined organic layers were washed with water, dried, filtered and evaporated. The residue was stirred in 2,2'-oxybispropane, filtered off and recrystallized from acetonitrile, yielding 11.7 g of ethyl 4-(10H-imidazo[ 1,2-a]thieno[3,2-d] azepin-10-ylidene)- 1-piperidinecarboxylate; mp. 193.5° C. (comp. 19);

b) A mixture of 11.7 g of compound (19), 19.0 g of potassium hydroxide and 170 ml of 2-propanol was stirred for 6 hours at reflux temperature. The reaction mixture was evaporated and the residue was taken up in water and neutralized with acetic acid. The product was extracted with dichloromethane and the extract was dried, filtered and evaporated. The residue was purified by column chromatography (silica gel; $CH_2Cl_2$/CH $_3OH(NH_3)$ 95:5). The eluent of the desired fraction was evaporated and the residue was converted into the hydrochloride salt (1: 1) in acetonitrile. The salt was filtered off and dried, yielding 2.5 g (24.0%) of 10-(4-piperidinylidene)-10H-imidazo[1,2-a]-thieno[ 3,2-d]azepine monohydrochloride (comp. 28).

EXAMPLE 17

To a cooled mixture (ice-bath) of 22 g of the base of compound (6) and 500 ml of 1,2-dichloroethane were added dropwise, while cooling, 22 g of 1-chloroethyl chloroformate. After stirring for 1 hour at room temperature and for 2 hours at reflux temperature, the reaction mixture was evaporated. The residue was taken up in 500 ml of methanol and stirred for 1 hour at reflux temperature. The reaction mixture was evaporated again and the residue was taken up in water and basified with sodium hydroxide 50%. The product was extracted with dichloromethane and the extract was dried, filtered and evaporated. The residue was purified by column chromatography (silica gel; $CH_2Cl_2$/$CH_3OH(NH_3)$ 95:5→92:8). The eluent of the desired fraction was evaporated and the residue was converted into the cyclohexanesulfamic acid salt (1:1) in methanol. The salt was filtered off and dried, yielding 14.63 g (42.2%) of 6,10-dihydro-10-(4-piperidinylidene)-5H-imidazo[1,2-a] thieno[3,2-d]azepine cyclohexylsulfamate (1:1); mp.<250° C. (decorap.) (comp. 17).

EXAMPLE 18

A mixture of 6.8 g of compound (31) and 200 ml of methanol was hydrogenated at normal pressure and at room temperature in the presence of 2 g of palladium-on-charcoal catalyst 10%. After the calculated amount of hydrogen was taken up, the catalyst was filtered off and the tiltrate was evaporated. The residue was stirred in 2,2'-oxybispropane. The precipitate was filtered off and dried, yielding 4.5 g (84.8%) of (±) 5,6,7,10-tetrahydro-7-methyl-10-(4-piperidinyl)imidazo[ 1,2-a]pyrrolo[ 3,2-d]-azepine hemihydrate; 121.6° C. (comp. 36).

EXAMPLE 19

A mixture of 2.75 g of 6-(2-chloroethyl)-7-methyl-5H-thiazolo[3,2-a]pyrimidin-5-one, 3.1 g of the base of compound (1), 1.6 g of sodium carbonate and 100 ml of 4-methyl- 2-pentanone was stirred for 72 hours at reflux temperature. After cooling, water was added and the whole was stirred. The separated aqueous layer was extracted with dichloromethane. The combined organic layers were dried, filtered and evaporated. The residue was purified by column chromatography (silica gel; $CH_2Cl_2$/$CH_3OH$ 95:5→ $CH_2Cl_2$/$CH_3OH(NH_3)$ 95:5). The eluent of the desired fraction was evaporated and the residue was crystallized from acetonitrile. The precipitate was filtered off and dried, yielding 1.70 g (32.7%) of 6-[2-[4-(5,6-dihydro-7-methyl-10(7H)-imidazo[ 1,2-a]-pyrrolo]3,2-d]azepin-10-ylidene)-1-piperidinyl]ethyl]-7-methyl-5H-thiazolo[3,2-a]-pyrimidin- 5-one; mp. 201.4° C. (comp. 5).

EXAMPLE 20

A mixture of 1.2 g of 2-ethenylpyridine, 2.7 g of the base of compound (1) and 150 ml n-butanol was stirred overnight at reflux temperature. The reaction mixture was evaporated and the residue was purified by column chromatography (silica gel; $CH_2Cl_2$/$CH_3OH$ 90:10). The eluent of the desired fraction was evaporated and the residue was converted into the (E)-butenedioate salt (1:1) in 2-propanol. The salt was filtered off and dried, yielding 0.81 g (16%) of 5,6,7,10-tetrahydro-7-methyl-10-[1-[2-(2-pyridinyl)-ethyl]-4-piperidinylidene]imidazo[ 1,2-a ]pyrrolo[3,2-d]azepine hemihydrate (E)-2-butenedioate (1:1); mp. 172.9° C. (comp. 53).

EXAMPLE 21 a) A mixture of 2 g of compound (36), 1 g of polyoxymethylene, 150 ml of methanol and 1 ml of a solution of thiophene in methanol (4%) was hydrogenated at normal pressure and at 50° C. in the presence of 1 g of palladium-on-charcoal catalyst 10%. After the calculated amount of hydrogen was taken up, the catalyst was filtered off and the filtrate was evaporated. The residue was taken up in water and there was added $NH_4OH$(aq.). The whole was stirred for 30 minutes and the product was extracted 3 times with dichloromethane. The combined organic layers were dried, filtered and evaporated. The residue was stirred in 2,2'-oxybispropane, yielding 1.4 g (70%) of (35 )-5,6,7,10-tetrahydro-7-methyl-10-(1-methyl-4-piperidinyl)imidazo[ 1,2-a]pyrrolo-[ 3,2-d]azepine; mp. 163.9° C. (comp. 37).

b) A mixture of 4.0 g of compound (1), 15 ml of 2-propanone and 30 ml of acetic acid was stirred for 2 hours at room temperature under nitrogen atmosphere. 2.25 g of sodium tetrahydroborate was added portionwise during 30 minutes. After stirring overnight at room temperature, the reaction mixture was decomposed with water and treated with a sodium hydroxide solution 15%. The product was extracted with dichloromethane. The extract was dried, filtered and evaporated. The residue was purified by column chromatography (silica gel; $CH_2Cl_2$/$CH_3OH(NH_3)$ 96:5). The eluent of the desired fraction was evaporated and the residue was crystallized from acetonitrile. The product was filtered off and dried, yielding 3.06 g (67%) of 5,6,7,10-tetra-hydro- 7-methyl-10-[1-(1-methylethyl)-4-piperidinylidene]imidazo[1,2-a]pyrrolo[3,2-d]-azepine; mp. 178.3° C. (comp. 88).

EXAMPLE 22

Through a stirred mixture of 8.8 g of the base of compound (1) and 200 ml of methanol was bubbled oxirane for 3 hours. The reaction mixture was evaporated and the residue was purified by column chromatography (silica gel; $CH_2Cl_2$/$CH_3OH(NH_3)$ 95:5). The eluent of the desired fraction was evaporated and the residue was converted into the (E)-butenedioate salt (1:1) in ethanol. The salt was filtered off and dried, yielding 6.43 g (45.9%) of 4-(5,6,7, 10-tetrahydro-7-methylimidazo[1,2-a]pyrrolo[3,2-d]azepin-10-ylidene) -1-piperidineethanol (E)-2-butenedioate(1:1) hemihydrate; mp. 210.3° C. (comp. 64).

EXAMPLE 23

To a stirred mixture of 0.58 g of a dispersion of sodium hydride in mineral oil (50%) and 100 ml of N,N-dimethylacetamide at room temperature and under a nitrogen atmosphere were added portionwise 2.7 g of compound (10). After stirring for 1 hour at room temperature, the mixture was cooled to 0° C. and a solution of 0.79 g of acetyl chloride in N,N-dimethylacetamide was added dropwise (0° C.). Then, the whole was stirred overnight at room temperature and the mixture was poured into a mixture of sodium hydrogen carbonate in water. The product was extracted with dichloromethane and the extract was dried, filtered and evaporated. The residue was purified by column chromatography (silica gel; $CH_2Cl_2$/$CH_3OH(NH_3)$ 97:3). The eluent of the desired fraction was evaporated and the residue was crystallized from acetonitrile, yielding 0.37 g (12%) of 7-acetyl-5,6,7,10-tetrahydro-10-(1-methyl-4-piperidinylidene)imidazo- [1,2-a]pyrrolo[3,2-d]azepine; mp. 198.0° C. (comp. 30).

EXAMPLE 24

To 40 ml of N,N-dimethylformamide were added dropwise while cooling 6.15 g of phosphoryl chloride. After stirring for 30 minutes there were added portionwise 8.5 g of compound (2) while cooling. The temperature raised up to 30° C. and the mixture was stirred for 1 hour. The reaction mixture was cooled to room temperature, poured into ice water and basified with potassium carbonate. The product was extracted with dichloromethane and the extract was dried, filtered and evaporated. The residue was purified by column chromatography (silica gel; $CH_2Cl_2/CH_3OH$ 95:5; $CH_2Cl_2/CH_3OH(NH_3)$ 95:5). The eluent of the desired fraction was evaporated and the residue was crystallized from acetonitfile. The product was filtered off and dried, yielding 5.41 g (58%)of 5,6,7,10-tetrahydro-7-methyl-10-(1-methyl-4-piperidinylidene)imidazo[1,2-a]-pyrrolo[ 3,2-d]azepine-8-carboxaldehyde; top. 203.2° C. (comp. 12).

EXAMPLE 25

To a mixture of 3 g of compound (12) in 100 ml of methanol were added portionwise 3 g of sodium tetrahydroborate. After stirring for 1 hour, the reaction mixture was evaporated and the residue was taken up in water. The product was extracted with dichloromethane and the extract was dried, filtered and evaporated. The residue was purified by column chromatography (silica gel; $CH_2Cl_2$/ $CH_3OH(CH_3)$ 93:7→90:10). The eluent of the desired fraction was evaporated and the residue was boiled in acetonitrile. The product was filtered off and dried, yielding 1.27 g (42.8%) of 5,6,7,10-tetrahydro-7-methyl-10-(1-methyl-4-piperidinylidene)imidazo[ 1,2-a]pyrrolo-[ 3,2-d]azepine-8-methanol; mp. 213.8° C. (comp. 13).

EXAMPLE 26

To a stirred solution of 6 g of compound (12) in 100 ml of water was added dropwise a solution of 6 g of potassium hydroxide in 40 ml of water. Then, there was added dropwise a solution of 6 g of silver nitrate in 40 ml of water while heating till 60° C. and the mixture was stirred for 24 hours at 60° C. The mixture was filtered over diatomaceous earth and washed twice with water. The flitrate was washed three times with dichloromethane and the aqueous layer was stirred up with activated charcoal. The mixture was filtered over diatomaceous earth and evaporated till ±60 ml and purified by column chromatography (HPLC Lichroprep RP-18; $H_2O/CH_3CN$ 95:5). The eluent of the desired fraction was evaporated and the residue was recrystallized from a mixture of acetonitrile and water. The residue was recrystallized from water and treated with activated charcoal, yielding 1.6 g (24%) of 5,6,7,10-tetrahydro-7-methyl-10-(1-methyl- 4-pipefidinylidene) imidazo[1,2-alpyrrolo[3,2-d] azepine-8-carboxylic acid monohydrate; mp. 209.0° C. (comp. 87).

EXAMPLE 27 a) A mixture of 1.55 g of compound (12), 1.32 g of β-ethoxy-β-oxopropanoic acid, 0.1 ml of piperidine and 30 ml of pyridine was stirred for 8 hours at reflux temperature. The reaction mixture was evaporated and the residue was poured into water. The product was extracted with dichloromethane and the extract was dried, filtered and evaporated. The residue was purified by column chromatography (silica gel; $CH_2Cl_2/CH_3OH(NH_3)$ 95:5). The eluent of the desired fraction was evaporated and the residue was dried, yielding 1.7 g (89.4%) of ethyl (E)-3-[5,6,7,10-tetrahydro-7-methyl-10-(1-methyl- 4-piperidinylidene)imidazo[1,2-a]pyrrolo[3, 2-d]azepin-8-yl]-2-propenoate (comp. 43);

b) To a mixture of 1.7 g of compound (43) and 20 ml of tetrahyclrofuran was added dropwise a solution of 0.56 g of potassium hydroxide in 50 ml of water. After stirring overnight, the reaction mixture was washed twice with dichloromethane. After neutralizing, the mixture was purified by column chromatography (HPLC Lichroprep RP 18 ;eluent 1) $H_2O$ 100%; 2)$CH_3CN$ 100% 3)CH3OH)). The eluent of the desired fraction was evaporated and the residue was crystallized from a mixture of acetonitrile and 4-methyl-2-pentanone. The crystals were filtered off and dried, yielding 0.4 g (21.1%) of (E)-3-[5,6,7,10-tetrahydro-7-methyl-10-(1-methyl-4-piperidinylidene)-imidazo[ 1,2-a]pyrrolo[3,2-d] azepin-8-yl]-2-propenoic acid sesquihydrate; mp. 220.0° C. (comp. 44).

EXAMPLE 28

A mixture of 5.6 g of compound (2), 3.6 g of 1-bromo-2,5-pyrrolidinedione and 50 ml of N,N-dimethylformamide was stirred overnight at room temperature. Then, the reaction mixture was poured into ice water and basified with potassium carbonate. The product was extracted three times with dichloromethane. The combined organic layers were dried, filtered and evaporated. The residue was purified by column chromatography (silica gel; $CH_2Cl_2/CH_3OH(CH_3)$ 95:5). The eluent of the desired fraction was evaporated and the residue was taken up in water and basified with sodium hydroxide 50%. The product was extracted with dichloromethane and the extract was dried, filtered and evaporated. The residue was recrystallized from a mixture of acetonitrile and 2,2'-oxybispropane (1/10), yielding 1.7 g (23.5%) of 8-bromo 5,6,7, 10-tetrahydro-7-methyl-10-(1-methyl-4-piperidinyl idene )imidazo[ 1,2-a]-pyrrolo[3,2-d]azepine; mp. 179.2° C. (comp. 42).

EXAMPLE 29

A mixture of 3 g of compound (16) and 400 ml of methanol saturated with ammonia was hydrogenated and normal pressure and at 20° C in the presence of 1 g of Raney Nickel. After the calculated amount of hydrogen was taken up, the catalyst was filtered off and the tiltrate was evaporated, yielding 4 g (100%) of 4-(5,6,7,10-tetrahydro-7-methyl-imidazo[ 1,2-alpyrrolo[3,2-dlazepin-10-ylidene)-1-piperidineethanamine (comp. 26).

EXAMPLE 30

A mixture of 1 g of 2-chloropyrimidine, 3 g of compound (26), 0.8 g of sodium hydrogen carbonate and 100 ml of ethanol was stirred overnight at reflux temperature. After cooling, the reaction mixture was evaporated and the residue was dissolved in dichloromethane, washed with water, dried, filtered and evaporated. The residue was purified by column chromatography (silica gel; $CH_2Cl_2/CH_3OH$ 95:5→90: 10). The eluent of the desired fraction was evaporated and the residue was boiled in 2-propanol and converted into the (E)-2-butenedioate salt. The salt was dissolved in water and basified with sodium hydroxide 50% and the product was extracted with dichloromethane. The extract was dried, filtered and evaporated. Then 100 ml of a 3 % NaOH-solution and 50 ml of 1,4-dioxane were added and the whole was stirred overnight at room temperature. The mixture was extracted three times with methylbenzene and twice with dichloromethane. The combined organic layers were dried, filtered and evaporated. The residue was recrystallized from acetonitrile, yielding 1.4 g (35.9%) of N-[2-[4( 5,6,7, 10-tetrahydro-7-methylimidazo[ 1,2-a]pyrrolo[ 3,2-d]azepin-10-ylidene)-1-piperidinyl] ethyl]-2-pyrimidinamine; mp. 202.0° C. (comp. 27).

EXAMPLE 31 a) A mixture of 4.64 g of ethyl 2,5-diethoxytetrahydro-2-furancarboxylate, 4.1 g of compound (26) and 100 ml of acetic acid was stirred for 2 hours at 80° C. The reaction mixture was evaporated and the residue was taken up in water and basified with potassium carbonate. The product was extracted with dichloromethane and the extract was dried, filtered and evaporated. The residue was purified by column chromatography (silica gel; $CH_2Cl_2/C_2H_5OH$ 96:4→92:8). The eluent of the desired fraction was evaporated and the residue was crystallized from acetonitrile, yielding 2.35 g (41%) of ethyl 1-[2-[4-(5,6,7,10-tetrahydro-7-methylimidazo[ 1,2-a]pyrrolo[ 3,2-d]azepin- 10-ylidene)-1-piperidinyl]ethyl]-1H-pyrrole-2-carboxylate; mp. 161.5° C. (comp. 80).

b) A mixture of 1.65 g of compound (80), 25.0 ml of a sodium hydroxide solution 1N, 100 ml of water and 40 ml of tetrahydrofuran was stirred and refluxed over weekend. The reaction mixture was washed with dichloromethane and treated with 25 ml of a hydrochloric acid solution 1.0N. The product was extracted with dichloromethane. The extract was dried, filtered and evaporated. The residue was crystallized from methanol, yielding 0.3 g (19.5%)of 1-[2-[4-(5,6,7,10-tetrahydro-7-methylimidazo[ 1,2-a]pyrrolo[3,2-d]azepin-10-ylidene )-1-piperidinyl]ethyl]-1H-pyrrole-2-carboxylic acid (comp. 89).

EXAMPLE 32

To a stirred mixture of 1.1 g of 3-furancarboxylic acid, 2 g of N,N-diethylethanamine and 150 ml of dichloromethane were added 2.6 g of 2-chloro-1-methylpyridium iodide. After stirring for 1 hour at room temperature, there were added 3.1 g of compound (26) and stirring was continued for 3 hours. Then the mixture was washed with water and the organic layer was separated, dried, filtered and evaporated. The residue was purified by column chromatography (silica gel; $CH_2Cl_2/CH_3OH(NH_3)$ 95:5). The eluent of the desired fraction was evaporated and the residue was suspended in 2,2'-oxybispropane. The precipitate was filtered off and dried, yielding 1.82 g (44%) of N-[2-[4-( 5,6,7,10-tetrahydro-7-methylimidazo[1,2-alpyrrolo[3,2-d]azepin-10-ylidene)-1-piperidinyl] ethyl]-3-furancarboxamide hemihydrate; mp. 138.1 ° C. (comp. 50).

EXAMPLE 33

A mixture of 0.7 g of methyl isocyanate, 3.1 g of compound (26) and 150 ml of tetrahydrofuran was stirred overnight at room temperature. The mixture was evaporated and the residue was purified by column chromatography (silica gel; $CH_2Cl_2/CH_3OH(NH_3)$ 95:5). The eluent of the desired fraction was evaporated and the residue was suspended in 2,2'-oxybispropane. The product was filtered off and dried, yielding 0.84 g (22%) of N-methyl-N'-[2-[4-(5,6,7,10-tetrahydro-7-methylimidazo[ 1,2-a]-pyrrolo[ 3,2-d] azepin-10-ylidene)-1-piperidinyllethyl]urea hemihydrate; mp. 126.2° C. (comp. 52).

EXAMPLE 34 a) A mixture of 6.4 g of methyl N-(2,2-dimethoxyethyl)-N'-methylcarbamimidothioate monohydroiodide, 6.2 g of compound (26) and 150 ml of 2-propanol was stirred overnight at reflux temperature. The reaction mixture was evaporated, yielding 9.1 g (100%) of N-(2,2-dimethoxyethyl)-N"-methyl-N"-[ 2-[ 4-(5,6,7,10-tetrahydro-7-methylimidazo[ 1,2-a]pyrrolo[3,2-d]azepin-10-ylidene)-1-piperidinyl]ethyl]guanidine (comp. 59).

b) A mixture of 9.1 g compound (59) and 150 ml of hydrochloric acid 10% was stirred for 2 hours at reflux temperature. The reaction mixture was poured into ice and basified with sodium hydroxide. The product was extracted with dichloromethane and the extract was dried, filtered and evaporated. The residue was purified by column chromatography (silica gel; methylbenzene/1,4-dioxane/$CH_3OH$/$NH_4OH$ 45:25:25:5). The eluent of the desired fraction was evaporated and the residue was converted into the (E)-2-butenedioate salt (1:2) in ethanol. The salt was filtered off and dried, yielding 1.18 g (9%) of N-(1-methyl-1H-imidazol-2-yl)-4-(5,6,7,10-tetrahydro-7-methyl-imidazo[ 1,2-a ]pyrrolo[3,2-d]azepin-10-ylidene)-1-piperidineethanamine (E)-2-butenedioate salt (1:2) hemiethanolate; mp. 222.4° C. (comp. 60).

EXAMPLE 35 a) To a stirred mixture of 9.6 g of carbon disulfide, 3.3 g of (dicyclohexyl)carbodiimide and 100 ml of tetrahydrofuran at −10° C. was added dropwise a solution of 5 g of compound (26) in tetrahydrofuran (temp. −10° C.). After stirring for 1 hour at room temperature, the reaction mixture was evaporated, yielding 5.6 g (100%) of 5,6,7,10-tetrahydro- 10-[1-(2oisothiocyanatoethyl)-4-piperidinylidene]-7-methylimidazo[ 1,2-a]-pyrrolo[ 3,2-d]azepine (comp. 83);

b) A mixture of 1.75 g 2,3-pyridinedione, 5.6 g of compound (83) and 150 ml of tetrahydrofuran was stirred overnight at reflux temperature. The reaction mixture was evaporated, yielding 7.3 g (100%)of N-(4-amino-3-pyridinyl)-N'-[2-[4-(5,6,7,10- tetrahydro-7-methylimidazo[1,2-a] pyrrolo[3,2-d]azepin-10-ylidene)-1-piperidinyl]ethyl] thiourea (comp. 84);

c) A mixture of 7.3 g of compound (84), 4.6 g of mercury(II)oxide, a few crystals of sulfur powder and 150 ml of methanol saturated with ammonia was stirred for 2 hours at reflux temperature. The reaction mixture was filtered over diatomaceous earth and evaporated. The residue was purified by column chromatography (silica gel; $CH_2Cl_2/CH_3OH(NH_3)$ 90: 10). The eluent of the desired fraction was evaporated and the residue was suspended in 2,2'-oxybispropane. The product was filtered off and dried, yielding 1.47 g (21.4%) of N-[2-[4-(5,6,7,10-tetrahydro-7-methylimidazo[1,2-a]-pyrrolo[ 3,2-d]azepin-10-ylidene )-1-pipeddinyl]ethyl]-1H-imidazo[ 4,5-c]pyridin-2-amine hemihydrate; mp. 175.2° C. (comp. 85).

EXAMPLE 36

A mixture of 2.2 g of 1 H-1-methyl-2-imidazothiol, 7.1 g of compound (73), 2.7 g of potassium carbonate and 200 ml of 2-propanone was stirred for 8 hours at reflux temperature. The reaction mixture was evaporated and the residue was taken up in water. The product was extracted with dichloromethane and the extract was dried, filtered and evaporated. The residue was purified by column chromatography (silica gel; $CH_2Cl_2/CH_3OH(NH_3)$ 95:5). The eluent of the desired fraction was evaporated and the residue was crystallized from acetonitrile. The product was filtered off and dried, yielding 0.87 g (11%) of 5,6,7, 10-tetrahydro-7-methyl-10-[1-[2-[(1-methyl-1H -imidazol-2-yl)thio]ethyl]-4-piperidinylidene]imidazo[ 1,2-a]pyrrolo[ 3,2-d]azepine; mp. 199.5° C. (comp. 74).

EXAMPLE 37

To a solution of 3.7 g of compound (68) in 10 ml of tetrahydrofuran was added dropwise a solution of 0.6 g of potassium hydroxide in 30 ml of water. After stirring overnight at room temperature, the reaction mixture was evaporated and the aqueous layer was washed twice with dichloromethane. The aqueous layer was treated with activated charcoal, filtered over diatomaceous earth and neutralized with hydrochloric acid 5N. The precipitate was filtered off and dried, yielding 2 g (57%) of 4-(5,6,7,10-tetrahydro-7-methylimidazo[1,2-a]pyrrolo[3,2-d]azepin-10-ylidene)-1-piperidinepropanoic acid hemihydrate; mp.> 260° C. (comp. 69).

EXAMPLE 38

A mixture of 1.3 g of compound (55), 5 ml of acetic acid, 5 ml of sulphuric acid and 5 ml of water was stirred for 2 hours at reflux temperature. The mixture was poured into ice water and basified with NH4OH. The product was extracted with dichloromethane and the extract was dried, filtered and evaporated. The residue was purified by column chromatography (silica gel; $CH_2Cl_2/CH_3OH(NH_3)$ 90:10). The eluent of the desired fraction was evaporated and the residue was crystallized from acetonitrile, yielding 0.33 g (24.6%) of 4-[2-[4-(5,6-dihydro-10H-imidazo[1,2-a]thieno[3,2-d]azepin-10-ylidene)-1-piperidinyl]ethyl]benzamide; mp. 196.0° C. (comp. 57).

All compounds listed in Tables 1-3 were prepared following methods of preparation described in examples 9-38, as is indicated in the column Ex. No.

TABLE 1

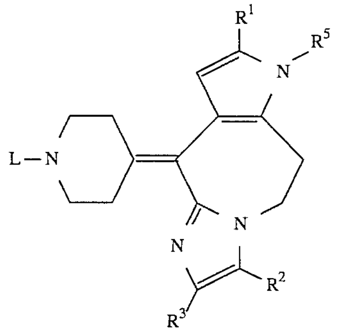

| Co. No. | Ex. No | $R^1$ | $R^2$ | $R^3$ | $R^5$ | L | physical data/ mp. (°C.) |
|---|---|---|---|---|---|---|---|
| 1 | 10 | H | H | H | $-CH_3$ | H | (E)-butenedioate (1:2)/206.0 |
| 2 | 9 | H | H | H | $-CH_3$ | $-CH_3$ | 186.8 |
| 4 | 16a | H | H | H | $-CH_3$ | $-CO-O-C_2H_5$ | 232.0 |
| 5 | 19 | H | H | H | $-CH_3$ | 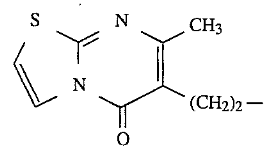 | 201.4 |
| 7 | 9 | H | H | $-CH_3$ | $-CH_3$ | $-CH_3$ | 189.1 |
| 8 | 9 | H | $-CH_3$ | H | $-CH_3$ | $-CH_3$ | 279.8 |
| 10 | 9 | H | H | H | H | $-CH_3$ | 221.6 |
| 11 | 17 | H | H | $-CH_3$ | $-CH_3$ | H | cyclohexyl-sulfamate (1:3) |
| 12 | 24 | $-CHO$ | H | H | $-CH_3$ | $-CH_3$ | 203.2 |
| 13 | 25 | $-CH_2OH$ | H | H | $-CH_3$ | $-CH_3$ | 213.8 |
| 14 | 24 | $-CHO$ | $-CH_3$ | H | $-CH_3$ | $-CH_3$ | 244.3 |
| 15 | 25 | $-CH_2OH$ | $-CH_3$ | H | $-CH_3$ | $-CH_3$ | 258.4 |
| 16 | 19 | H | H | H | $-CH_3$ | $-CH_2-CN$ | 181.0 |
| 22 | 19 | H | H | H | $-CH_3$ | $-(CH_2)_2$-(4-$H_3CO-C_6H_4$)$-$ | ethanedioate (2:5), $H_2O$/165.4 |
| 26 | 29 | H | H | H | $-CH_3$ | $-(CH_2)_2-NH_2$ | |
| 27 | 30 | H | H | H | $-CH_3$ | 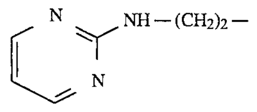 | 202.0 |
| 29 | 19 | H | H | H | $-CH_3$ | 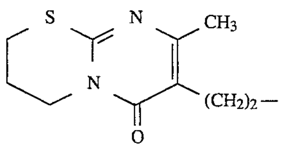 | (E)-butenedioate (1:2), $H_2O$/216.5 |
| 30 | 23 | H | H | H | $-CO-CH_3$ | $-CH_3$ | 198.0 |
| 31 | 9 | H | H | H | $-CH_3$ | $-CH_2-C_6H_5$ | 211.3 |

TABLE 1-continued

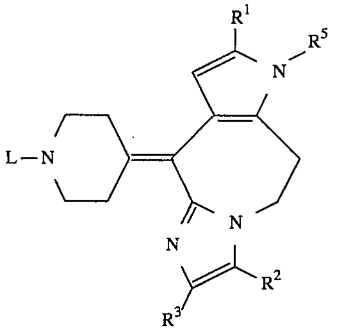

| Co. No. | Ex. No | $R^1$ | $R^2$ | $R^3$ | $R^5$ | L | physical data/ mp. (°C.) |
|---|---|---|---|---|---|---|---|
| 32 | 19 | H | H | H | $-CH_3$ | 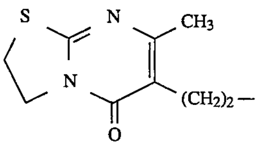 | (E)-butenedioate (2:3)/254.8 |
| 33 | 19 | H | H | H | $-CH_3$ | $-(CH_2)_2-O-C_2H_5$ | 167.9 |
| 34 | 19 | H | H | H | $-CH_3$ | 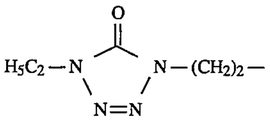 | 208.2 |
| 38 | 19 | H | H | H | $-CH_3$ | 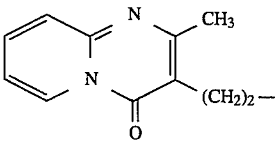 | (E)-butenedioate (1:1), $H_2O$/222.1 |
| 42 | 28 | Br | H | H | $-CH_3$ | $-CH_3$ | 179.2 |
| 43 | 27a | $-CH=CH-COOC_2H_5$ | H | H | $-CH_3$ | $-CH_3$ | (E) |
| 44 | 27b | $-CH=CH-COOH$ | H | H | $-CH_3$ | $-CH_3$ | (E)/3/2$H_2O$/220.0 |
| 50 | 32 | H | H | H | $-CH_3$ | 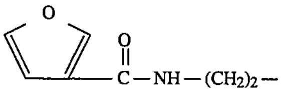 | ½ $H_2O$/138.1 |
| 52 | 33 | H | H | H | $-CH_3$ | $-(C_2)_2-NH-CO-NH-CH_3$ | ½ $H_2O$/126.2 |
| 53 | 20 | H | H | H | $-CH_3$ | 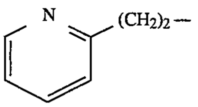 | (E)-2-butenedioate (1:1), 1/2 $H_2O$/ 172.9 |
| 56 | 30 | H | H | H | $-CH_3$ | 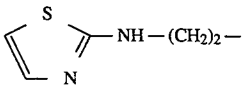 | (E)-2-butenedioate (1:1), 1/2 $H_2O$/ 204.0 |
| 58 | 19 | H | H | H | $-CH_3$ | 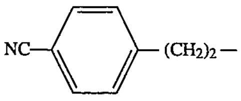 | 213.6 |
| 59 | 34a | H | H | H | $-CH_3$ | $-(CH_2)_2-NH-C(=N-CH_3)-NH-CH_2-CH-(OCH_3)_2$ | |

TABLE 1-continued

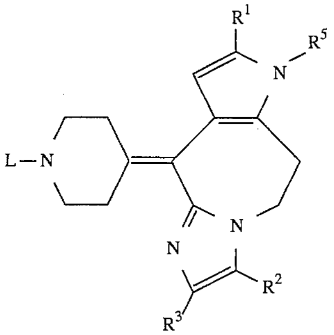

| Co. No. | Ex. No | $R^1$ | $R^2$ | $R^3$ | $R^5$ | L | physical data/ mp. (°C.) |
|---|---|---|---|---|---|---|---|
| 60 | 34b | H | H | H | $-CH_3$ | 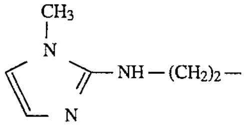 | (E)-butenedioate (1:2), 1/2 ethanol/ 222.4 |
| 61 | 9 | H | H | H | $-CH_3$ | $-CH_2-CH_3$ | (E)-butenedioate (1:1)/200.9 |
| 62 | 22 | H | H | H | $-CH_3$ | 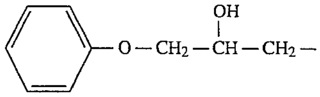 | 106.0 |
| 63 | 19 | H | H | H | $-CH_3$ | 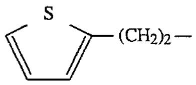 | (E)-2-butenedioate (1:1), 1/2 $H_2O$/ 195.5 |
| 64 | 22 | H | H | H | $-CH_3$ | $-(CH_2)_2-OH$ | (E)-2-butenedioate (1:1), ½ $H_2O$/ 210.3 |
| 65 | 19 | H | H | H | $-CH_3$ | 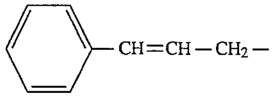 | (E)/201.5 |
| 66 | 19 | H | H | H | $-CH_3$ | 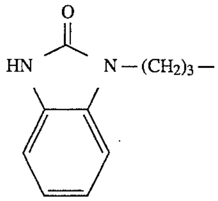 | (E)-butenedioate (2:3)/222.3 |
| 67 | 21a | H | H | H | $-CH_3$ | 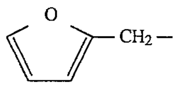 | 172.8 |
| 68 | 19 | H | H | H | $-CH_3$ | $-(CH_2)_2-CO-O-C_2H_5$ | (E)-butenedioate (1:1), ½ $H_2O$/ 164.9 |
| 69 | 37 | H | H | H | $-CH_3$ | $-(CH_2)_2-COOH$ | ½ $H_2O$/>260.0 |
| 70 | 19 | H | H | H | $-CH_3$ | 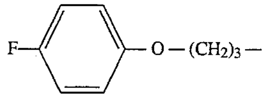 | (E)-butenedioate (2:3)/186.8 |
| 71 | 19 | H | H | H | $-CH_3$ | $-CH_2-CO-O-C_2H_5$ | 151.8 |
| 72 | 37 | H | H | H | $-CH_3$ | $-CH_2-COOH$ | $H_2O$/266.8 |
| 73 | 30 | H | H | H | $-CH_3$ | $-(CH_2)_2-O-SO_2-CH_3$ | |

TABLE 1-continued
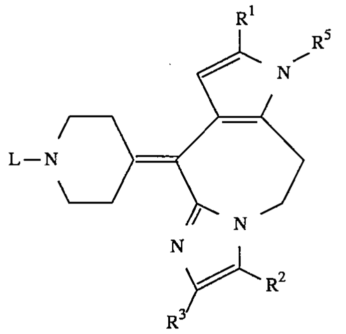
| Co. No. | Ex. No | $R^1$ | $R^2$ | $R^3$ | $R^5$ | L | physical data/ mp. (°C.) |
|---|---|---|---|---|---|---|---|
| 74 | 36 | H | H | H | $-CH_3$ | 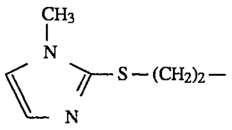 | 199.5 |
| 75 | 19 | H | H | H | $-CH_3$ | 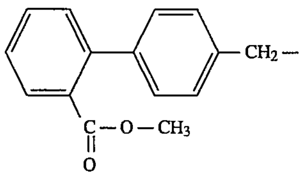 | 161.4 |
| 76 | 30 | H | H | H | $-CH_3$ | 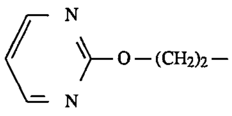 | 208.2 |
| 78 | 30 | H | H | H | $-CH_3$ | 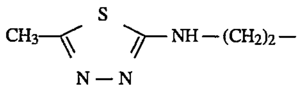 | 219.7 |
| 79 | 30 | H | H | H | $-CH_3$ | 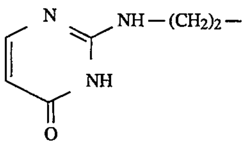 | (E)-butenedioate (1:2), 1/2 $H_2O$, 2-propanolate (1:1)/150.0 |
| 80 | 31a | H | H | H | $-CH_3$ | 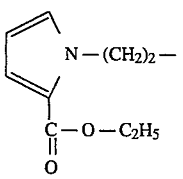 | 161.5 |
| 81 | 30 | H | H | H | $-CH_3$ | $-(CH_2)_2-O-CH_2-CO-O-C_2H_5$ | |
| 82 | 37 | H | H | H | $-CH_3$ | $-(CH_2)_2-O-CH_2-COOH$ | 2 $H_2O$/166.8 |
| 83 | 35a | H | H | H | $-CH_3$ | $-(CH_2)_2-NCS$ | |
| 84 | 35b | H | H | H | $-CH_3$ | 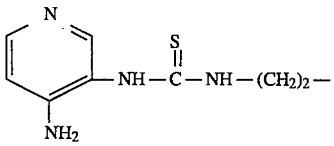 | |

TABLE 1-continued
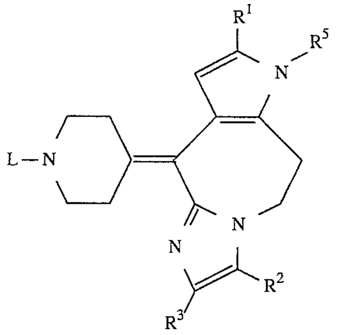
| Co. No. | Ex. No | $R^1$ | $R^2$ | $R^3$ | $R^5$ | L | physical data/ mp. (°C.) |
|---|---|---|---|---|---|---|---|
| 85 | 35c | H | H | H | $-CH_3$ | 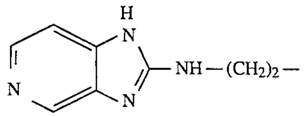 | ½ $H_2O$/175.2 |
| 86 | 37 | H | H | H | $-CH_3$ | 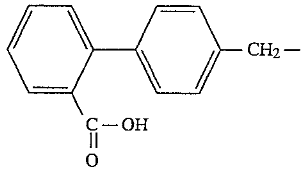 | $H_2O$/199.2 |
| 87 | 26 | $-COOH$ | H | H | $-CH_3$ | $-CH_3$ | $H_2O$/209.0 |
| 88 | 21b | H | H | H | $-CH_3$ | $-CH-(CH_3)_2$ | 178.3 |
| 89 | 31 | H | H | H | $-CH_3$ | 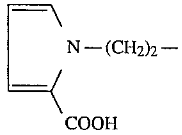 | ½ $H_2O$/172.0 |
| 90 | 36 | H | H | H | $-CH_3$ | 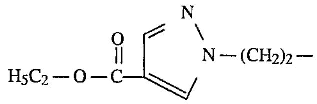 | mp. 150.7 |
| 91 | 31b | H | H | H | $-CH_3$ | 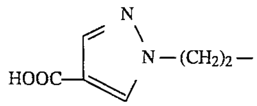 | mp. >260 |
TABLE 2
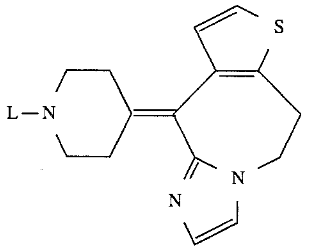
| Co. No. | Ex. No | L | physical data/ mp. (°C.) |
|---|---|---|---|
| 6 | 11 | $-CH_3$ | (E)-butenedioate (1:1)/227.2 |

TABLE 2-continued
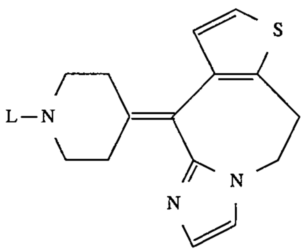
| Co. No. | Ex. No | L | physical data/ mp. (°C.) |
|---|---|---|---|
| 17 | 17 | H | cyclohexylsulfamate (1:1)/<250.0 |
| 21 | 16a | $-CO-O-C_2H_5$ | 185.5 |
| 40 | 19 | $-CO-CH_3$ | (E)-butenedioate (2:3), $H_2O$/136.6 |
| 23 | 19 | 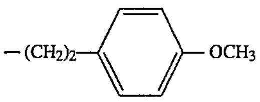 | ethanedioate (2:5), 1/2 $H_2O$/methanolate (2:1)/ 200.8 |
| 24 | 19 | 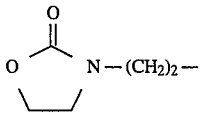 | ethanedioate (1:2), $H_2O$ (2:3)/200.2 |
| 25 | 19 | 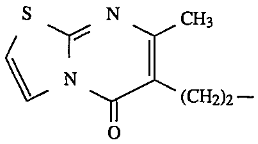 | HCl (1:3), $H_2O$ (2:3), ethanolate (2:1)/270.6 |
| 46 | 19 | 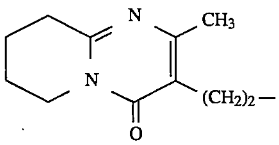 | (E)-2-butenedioate (2:3)/223.1 |
| 47 | 19 | 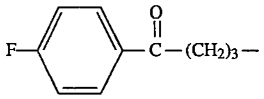 | (E)-2-butenedioate (1:1), 2-propanolate (2:1)/ 196.0 |
| 48 | 19 | $-CH_2-CH=CH_2$ | (E)-2-butenedioate (2:3), $H_2O$ (1:1) 159.3 |
| 49 | 19 | 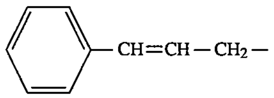 | ethanedioate (1:2), $H_2O$ (2:1)/154.9 |
| 54 | 22 | $-(CH_2)_2-OH$ | 179.2 |
| 55 | 19 | 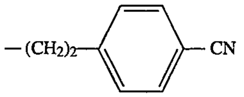 | ethanediate (1:2), 2-propanolate (2:1), $H_2O$ (2:1)/ 145.0 |
| 57 | 38 | 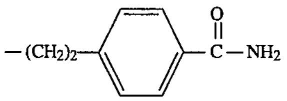 | 196.0 |
| 77 | 13 | 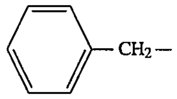 | 177.7 |
| 92 | 37 | $-CH_2-COOH$ | $H_2O$ (3:2)/214.9 |

TABLE 2-continued

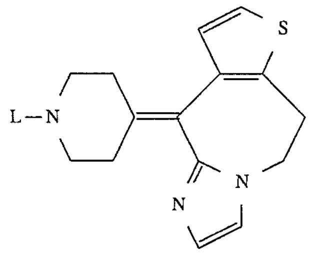

| Co. No. | Ex. No | L | physical data/ mp. (°C.) |
|---|---|---|---|
| 93 | 19 | $-CH_2-CO-O-C_2H_5$ | |
| 94 | 37 | $-(CH_2)_2-COOH$ | $H_2O$ (1:1)/230.6 |
| 95 | 19 | $-(CH_2)_2-CO-O-C_2H_5$ | |

TABLE 3

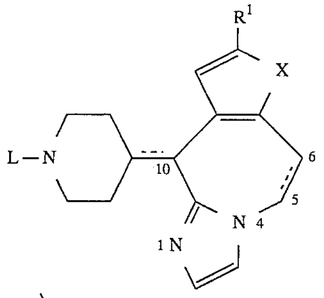

| Co. No. | Ex. No | X | $R^1$ | $C_5$---$C_6$ | 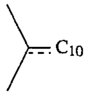 | L | physical data/ mp. (°C.) |
|---|---|---|---|---|---|---|---|
| 9 | 14 | S | H | d | d | $-CH_3$ | 136.4 |
| 18 | 12 | $N-CH_3$ | H | d | s | $-CH_3$ | 143.1 |
| 19 | 16a | S | H | d | d | $-CO-O-C_2H_5$ | 193.5 |
| 20 | 13 | O | H | s | d | $-CH_3$ | (E)-2-butenedioate (1:2) $H_2O$ (1:1)/156.4 |
| 28 | 16b | S | H | d | d | H | HCl (1:1) |
| 35 | 19 | S | H | d | d | 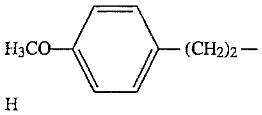 | ethanedioate (2:5), $H_2O$ (1:1)/172.7 |
| 36 | 18 | $N-CH_3$ | H | s | s | H | $H_2O$ (2:1)/121.6 |
| 37 | 21 | $N-CH_3$ | H | s | s | $-CH_3$ | 163.9 |
| 39 | 19 | S | H | d | d | 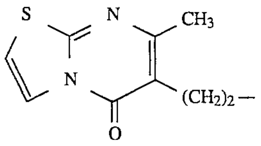 | ethanedioate (1:2), $H_2O$ (2:1)/259.0 |
| 41 | 15 | S | H | d | s | $-CH_3$ | HCl (1:2), $H_2O$ (1:1) 240.9 |
| 45 | 19 | $N-CH_3$ | H | s | s | 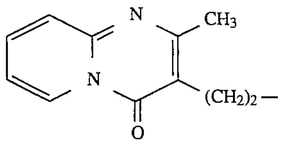 | (E)-2-butenedioate (2:3)/ 241.8 |
| 51 | 13 | O | $-CH_3$ | s | d | $-CH_3$ | (E)-2-butenedioate (1:1)/ 225.4 |

TABLE 3-continued

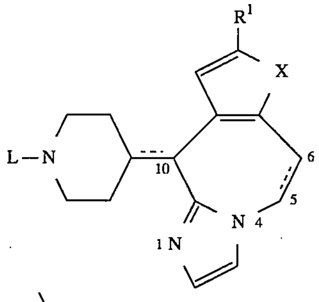

| Co. No. | Ex. No | X | $R^1$ | $C_5$=$C_6$ | 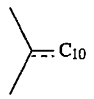 | L | physical data/ mp. (°C.) |
|---|---|---|---|---|---|---|---|

s = single bond
d = double bond

C. Composition Examples

The following formulations exemplify typical pharmaceutical compositions in dosage unit form suitable for systemic or topical administration to warm-blooded animals in accordance with the present invention. "Active ingredient" (A.I.) as used throughout these examples relates to a compound of formula (I) or a compound of formula (VI) wherein Q represents ($C_{1-6}$ alkyl or phenyl)oxycarbonyl, $C_{1-4}$ alkylcarbonyl or $C_{1-6}$ alkyl substituted with cyano or amino, a pharmaceutically acceptable acid addition salt or a stereochemically isomeric form thereof.

EXAMPLE 39

Oral Drops 500 g of the A.I. is dissolved in 0.5 l of 2-hydroxypropanoic acid and 1.5 l of the polyethylene glycol at 60°–80° C. After cooling to 30°–40° C. there are added 35 l of polyethylene glycol and the mixture is stirred well. Then there is added a solution of 1750 g of sodium saccharin in 2.5 l of purified water and while stirring there are added 2.5 l of cocoa flavor and polyethylene glycol q.s. to a volume of 50 l, providing an oral drop solution comprising 10 mg/ml of the A.I. The resulting solution is filled into suitable containers.

EXAMPLE 40

Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE 41

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE 42

Film-Coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90®) in about 200 ml of water. The wet powder mixture is sieved, dried and sieved again. Then there are added 100 g microcrystalline cellulose (Avicel®) and 15 g hydrogenated vegetable oil (Sterorex®). The whole is mixed well and compressed into tablets, giving 10.000 tablets, each comprising 10 mg of the active ingredient.

Coating

To a solution of 10 g methyl cellulose (Methocel 60 HG®) in 75 ml of denaturated ethanol there is added a solution of 5 g of ethyl cellulose (Ethocel 22 cps®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109®) and the whole is homogenated. The tablet cores are coated with the thus obtained mixture in a coating apparatus.

EXAMPLE 43

Injectable Solutions 1.8 g methyl 4-hydroxybenzoate and 0.2 g propyl 4-hydroxybenzoate are dissolved in about 0.5 l of boiling water for injection. After cooling to about 50° C. there are added while stirring 4 g lactic acid, 0.05 g propylene glycol and 4 g of the A.I. The solution is cooled to room temperature and supplemented with water for injection q.s. ad 1 l volume, giving a solution of 4 mg A.I. per ml. The solution is sterilized by filtration (U.S.P. XVII p. 811) and filled in sterile containers.

EXAMPLE 44

Suppositories 3 g A.I. is dissolved in a solution of 3 g 2,3-dihydroxybutanedioic acid in 25 ml polyethylene glycol 400.12 g surfactant (SPAN®) and triglycerides (Witepsol 5555®) q.s. ad 300 g are molten together. The latter mixture is mixed well with the former solution. The thus obtained mixture is poured into moulds at a temperature of 37°–38° C. to form 100 suppositories each containing 30 mg of the A.I.

We claim:

1. A compound of the formula:

(I)

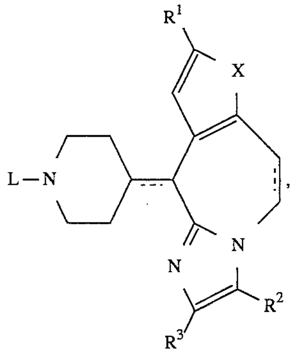

a pharmaceutically acceptable addition salt or a stereochemically isomeric form thereof, wherein: each of the dotted lines independently represents an optional bond;

$R^1$ represents hydrogen, $C_{1-4}$ alkyl, halo, ethenyl substituted with hydroxycarbonyl or $C_{1-4}$ alkyloxycarbonyl, hydroxy $C_{1-4}$ alkyl, formyl, hydroxycarbonyl or hydroxycarbonyl $C_{1-4}$ alkyl;

$R^2$ represents hydrogen, $C_{1-4}$ alkyl, ethenyl substituted with hydroxycarbonyl or $C_{1-4}$ alkyloxycarbonyl, $C_{1-4}$ alkyl substituted with hydroxycarbonyl or $C_{1-4}$ alkyloxycarbonyl, hydroxy $C_{1-4}$ alkyl, formyl or hydroxycarbonyl;

$R^3$ represents hydrogen, $C_{1-4}$ alkyl, hydroxy $C_{1-4}$ alkyl, phenyl or halo;

L represents hydrogen; $C_{1-6}$ alkyl; $C_{1-6}$ alkyl substituted with one substituent selected from the group consisting of hydroxy, halo, $C_{1-4}$ alkyloxy, hydroxycarbonyl, $C_{1-4}$ alkyloxycarbonyl, $C_{1-4}$ alkyloxycarbonyl $C_{1-4}$ alkyloxy, hydroxycarbonyl $C_{1-4}$ alkyloxy, $C_{1-4}$ alkyloxycarbonylamino, $C_{1-4}$ alkylaminocarbonyl, $C_{1-4}$ alkylaminocarbonylamino, $C_{1-4}$ alkylaminothiocarbonylamino, aryl, aryloxy and arylcarbonyl; $C_{1-4}$ alkyl substituted with both hydroxy and aryloxy; $C_{3-6}$ alkenyl; $C_{3-6}$ alkenyl substituted with aryl;

wherein each aryl is phenyl or phenyl substituted with halo, cyano, hydroxy, $C_{1-4}$ alkyl, $C_{1-4}$ alkyloxy, aminocarbonyl or phenyl substituted with $C_{1-4}$ alkyloxycarbonyl or hydroxycarbonyl; or L represents a radical of the formula:

—Alk—Y—$Het^1$ (a-1),

—Alk—NH—CO—$Het^2$ (a-2), or

—Alk—$Het^3$ (a-3);

wherein

Alk represents $C_{1-4}$ alkanediyl;

Y represents O, S or NH;

$Het^1$, $Het^2$ and $Het^3$ each represent:

furanyl, thienyl, oxazolyl, thiazolyl or imidazolyl each optionally substituted with one or two $C_{1-4}$ alkyl substituents;

pyrrolyl or pyrazolyl optionally substituted with formyl, hydroxy $C_{1-4}$ alkyl, hydroxycarbonyl, $C_{1-4}$ alkyloxycarbonyl or with one or two $C_{1-4}$ alkyl substituents;

thiadiazolyl or oxadiazolyl optionally substituted with amino or $C_{1-4}$ alkyl;

pyridinyl, pyrimidinyl, pyrazinyl or pyridazinyl each optionally substituted with $C_{1-4}$ alkyl, $C_{1-4}$ alkyloxy, amino, hydroxy or halo; or imidazo[4,5-c]pyridin-2-yl; and $Het^3$ may also represent a member selected from the group consisting of:

(a) 4,5-dihydro-5-oxo-1H-tetrazolyl substituted with $C_{1-4}$ alkyl;

(b) 2-oxo-3-oxazolidinyl;

(c) 2,3-dihydro-2-oxo-1H-benzimidazol-1-yl; and (d) a radical of the formula:

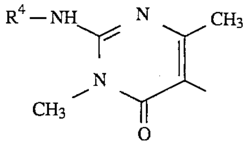

(b-1)

or

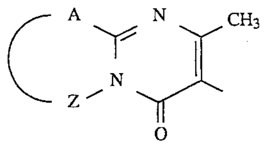

(b-2)

wherein:

$R^4$ represents hydrogen or $C_{1-4}$ alkyl;

A-Z represents S—CH=CH, S—$CH_2$—$CH_2$, S—$CH_2$—$CH_2$—$CH_2$, CH=CH—CH=CH, $CH_2$—$CH_2$—$CH_2$—$CH_2$, —N($CH_3$)—C($CH_3$)=CH— or —CH=C($CH_3$)—O—; and represents O, S or $NR^5$ wherein $R^5$ represents hydrogen, $C_{1-6}$ alkyl or $C_{1-4}$ alkylcarbonyl.

2. A compound according to claim 1 wherein is L is $C_{1-4}$ alkyl or $C_{1-4}$ alkyl substituted with hydroxycarbonyl or $C_{1-4}$ alkyloxycarbonyl.

3. A compound according to claim 1 wherein:

$R^1$ is hydrogen, $C_{1-4}$ alkyl, formyl, hydroxy $C_{1-4}$ alkyl or hydroxycarbonyl;

$R^2$ is hydrogen or $C_{1-4}$ alkyl;

$R^3$ is hydrogen or $C_{1-4}$ alkyl, and

L is hydrogen, $C_{1-4}$alkyl, propenyl, hydroxy $C_{1-4}$ alkyl, $C_{1-4}$ alkylaminocarbonylamino $C_{1-4}$ alkyl, phenyl $C_{1-4}$ alkyl, cyanophenyl $C_{1-4}$ alkyl, methoxyphenyl $C_{1-4}$ alkyl, hydroxyphenyl $C_{1-4}$ alkyl, aminocarbonylphenyl $C_{1-4}$ alkyl, hydroxycarbonyl $C_{1-4}$alkyl, $C_{1-4}$ alkyloxycarbonyl $C_{1-4}$ alkyl, or L is a radical of the formula:

—Alk—y—$Het^1$ (a-1),

—Alk—NH—CO—$Het^2$ (a-2), or

—Alk—$Het^3$ (a-3);

wherein $Het^1$, $Het^2$ and $Het^3$ each represent thienyl, furanyl, thiazolyl or imidazolyl each optionally substituted with $C_{1-4}$ alkyl; pyrimidinyl; hydroxypyrimidinyl or pyridinyl; and $Het^3$ may also represent a member selected from the group consisting of:

(a) 2-oxo-3-oxazolidinyl, (b) 4,5-dihydro-5-oxo-lH-tetrazolyl substituted with $C_{1-4}$alkyl, and (c) a radical of the formula:

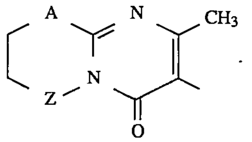

(b-2)

4. A compound according to claim 3 wherein $R^1$ is hydrogen, methyl or hydroxycarbonyl;

$R^2$ is hydrogen;

$R^3$ is hydrogen or methyl, and

L is hydrogen, $C_{1-4}$alkyl, propenyl, hydroxy $C_{1-4}$ alkyl, methylaminocarbonylamino-$C_{1-4}$ alkyl, hydroxycarbonyl $C_{1-4}$ alkyl, $C_{1-4}$ alkyloxycarbonyl $C_{1-4}$ alkyl, cyanophenyl $C_{1-4}$ alkyl or L is a radical of formula —Alk—Y—$Het^1$ (a-1), or —Alk—$Het^3$ (a-3);

wherein

Y is S or NH and $Het^1$ is imidazolyl substituted with methyl;

$Het^3$ is 2-oxo-3-oxazolidinyl; 4,5-dihydro-5-oxo-1 H-tetrazolyl substituted with ethyl; pyridinyl; thienyl; furanyl or a radical of the formula

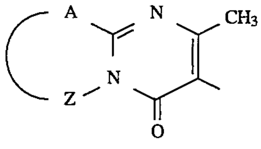

(b-2)

A-Z represents —S—CH=CH—, —S—$(CH_2)_2$—,—S—$(CH_2)_3$— or —$(CH_2)_4$—.

5. A compound according to claim 1 wherein said compound is selected from the group consisting of 6, 10-dihydro-7-methyl-10-(1-methyl-4-piperidinylidene)-5H, 7H-imidazo[ 1,2-a]-pyrrolo[3,2-d]azepine, 5,6-dihydro-10-(1-methyl-4-piperidinylidene)-10H-imidazo[1,2-a]thieno[ 3,2-d]azepine and 6,10-dihydro-8-methyl-10-(1-methyl-4 -piperidinylidene)-5H-furo[3,2-d]imidazo-[ 1,2-a]azepine, the stereoisomers and the pharmaceutically acceptable acid-addition salts thereof.

6. A compound having the formula

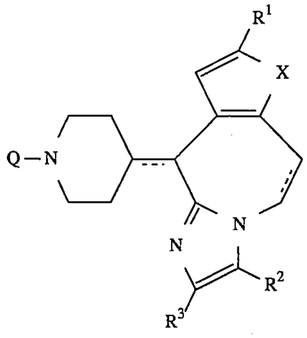

(VII)

a pharmaceutically acceptable addition salt or a stereochemically isomeric form thereof, wherein each of the dotted lines independently represents an optional bond;

X represents O, S or $NR^5$; $R^5$ represents hydrogen, $C_{1-6}$ alkyl or $C_{1-6}$ alkylcarbonyl;

$R^1$ represents hydrogen, $C_{1-4}$ alkyl, halo, ethenyl substituted with hydroxycarbonyl or $C_{1-4}$ alkyloxycarbonyl, hydroxy $C_{1-4}$ alkyl, formyl, hydroxycarbonyl or hydroxycarbonyl $C_{1-4}$ alkyl;

$R^2$ represents hydrogen, $C_{1-4}$alkyl, ethenyl substituted with hydroxycarbonyl or $C_{1-4}$ alkyloxycarbonyl, $C_{1-4}$ alkyl substituted with hydroxycarbonyl or $C_{1-4}$ alkyloxycarbonyl, hydroxy $C_{1-4}$ alkyl, formyl or hydroxycarbonyl;

$R^3$ represents hydrogen, $C_{1-4}$alkyl, hydroxy $C_{1-4}$alkyl, phenyl or halo;

Q represents ($C_{1-6}$ alkyl or phenyl)oxycarbonyl, $C_{1-4}$ alkylcarbonyl or $C_{1-6}$ alkyl substituted with halo, cyano, amino, isothiocyanato, (4-amino- 3-pyridinylaminothiocarbonylamino, $(CH_3O)_2CH—CH_2—NH—C(=NCH_3)—NH$, or methylsulfonyloxy.

7. A pharmaceutical composition comprising as an active ingredient a therapeutically effective amount of a compound as defined in claim 1 and a pharmaceutically acceptable carrier.

8. A pharmaceutical composition comprising as an active ingredient a therapeutically effective amount of. a compound as defined in claim 2 and a pharmaceutically acceptable carrier.

9. A pharmaceutical composition comprising as an active ingredient a therapeutically effective amount of a compound as defined in claim 3 and a pharmaceutically acceptable carrier.

10. A pharmaceutical composition comprising as an active ingredient a therapeutically effective amount of a compound as defined in claim 4 and a pharmaceutically acceptable carrier.

11. A pharmaceutical composition comprising as an active ingredient a therapeutically effective amount of a compound as defined in claim 5 and a pharmaceutically acceptable carrier.

12. A method of treating allergic conditions in warm blooded animals which comprises administering to warm blooded animals suffering from allergic conditions an effective anti-allergic amount of a compound as defined in claim 1.

13. A method of treating allergic conditions in warm blooded animals which comprises administering to warm blooded animals suffering from allergic conditions an effective anti-allergic amount of a compound as defined in claim 2.

14. A method of treating allergic conditions in warm blooded animals which comprises administering to warm blooded animals suffering from allergic conditions an effective anti-allergic amount of a compound as defined in claim 3.

15. A method of treating allergic conditions in warm blooded animals which comprises administering to warm blooded animals suffering from allergic conditions an effective anti-allergic amount of a compound as defined in claim 4.

16. A method of treating allergic conditions in warm blooded animals which comprises administering to warm blooded animals suffering from allergic conditions an effective anti-allergic amount of a compound as defined in claim 5.

* * * * *

UNITED STATES PATENT AND TRADEMARK OFFICE

CERTIFICATE OF CORRECTION

PATENT NO. : 5,461,050

DATED : October 24, 1995

INVENTOR(S) : Frans E. Janssens et al.

It is certified that error appears in the above-indentified patent and that said Letters Patent is hereby corrected as shown below:

At column 66, line 51, after "and" and before "represents" add --X--.

Signed and Sealed this

Seventeenth Day of December, 1996

Attest:

BRUCE LEHMAN

*Attesting Officer*

*Commissioner of Patents and Trademarks*